United States Patent [19]

Beltz et al.

[11] Patent Number: 4,753,873

[45] Date of Patent: Jun. 28, 1988

[54] PEPTIDES FOR THE DIAGNOSIS OF HTLV-III ANTIBODIES, THEIR PREPARATION AND USE

[75] Inventors: Gerald A. Beltz, Lexington; Richard M. Thorn, Milford; Dante J. Marciani, Hopkinton; Chung-Ho Hung, Milford; William A. Haseltine, Cambridge, all of Mass.

[73] Assignee: Cambridge Bioscience Corporation, Hopkinton, Mass.

[21] Appl. No.: 825,597

[22] Filed: Feb. 3, 1986

Related U.S. Application Data

[63] Continuation-in-part of Ser. No. 819,917, Nov. 6, 1985.

[51] Int. Cl.$^4$ .................. C12Q 1/70; G01N 33/53; G01N 33/577; C12N 15/00
[52] U.S. Cl. .................. 435/5; 424/86; 435/6; 435/7; 435/68; 435/172.3; 435/810; 435/240.27; 436/531; 436/548; 436/808; 436/811; 530/350; 530/388; 935/81; 935/109
[58] Field of Search .................. 435/5, 6, 7, 68, 172.3, 435/810, 240.27; 436/531, 548, 808, 811; 530/350, 388; 424/86; 935/81, 109, 110

[56] References Cited

U.S. PATENT DOCUMENTS

| | | | |
|---|---|---|---|
| 4,520,113 | 5/1985 | Gallo et al. | 436/504 |
| 4,595,654 | 6/1986 | Reckell et al. | 435/7 |
| 4,629,783 | 12/1986 | Cosand | 530/324 |
| 4,652,599 | 4/1987 | Gallo et al. | 435/239 |

FOREIGN PATENT DOCUMENTS

| | | |
|---|---|---|
| 0185444 | 6/1986 | European Pat. Off. |
| 0187041 | 7/1986 | European Pat. Off. |
| 86/01827 | 3/1986 | World Int. Prop. O. ............ 435/5 |
| 86/01834 | 3/1986 | World Int. Prop. O. ............ 435/5 |
| 86/04613 | 3/1986 | World Int. Prop. O. ............ 435/5 |
| 86/02930 | 5/1986 | World Int. Prop. O. ............ 435/5 |
| 86/04611 | 8/1986 | World Int. Prop. O. ............ 435/5 |

OTHER PUBLICATIONS

Kitchen et al., *Nature*, 312:367 (1984).
Kitchen et al., *J. Infect. Dis.* 153:788 (1986).
Samuel et al., *Science*, 226:194 (1985).
Ratner et al., *Nature*, 313:277-284 (1985).
Muessing et al., *Nature*, 313:450-458 (1985).
Sanchez-Pescador et al., *Science*, 227:484-492 (1985).
Wain-Hobson et al., *Cell*, 40:9-17 (1985).
Wong-Staal, et al., *Science*, 229:759-762 (1985).
Allan, et al., *Science*, 228:1091-1094 (1985).
Barin, et al., *Science*, 228:1094-1096 (1985).
Veronese, et al., *Science*, 229:1402-1405 (1985).
Chang, et al., *Bio Technology*, 3:905-909 (1985).
Chang, et al., *Science*, 228:93-96 (1985).
Crowl, et al., *Cell*, 41:979-986 (1985).
Cabradilla et al., *Bio Technology*, 4:128-133 (1985).
Chang et al, Nature, vol. 315, May 9, 1985, 151-4.

*Primary Examiner*—Christine M. Nucker
*Attorney, Agent, or Firm*—Saidman, Sterne, Kessler & Goldstein

[57] ABSTRACT

Certain peptide fragments of the human T-cell leukemia (lymphotropic) virus (HTLV-III) are particularly immunoreactive to HTLV-III antibodies, and can therefore be applied to immunodiagnostic tests for the detection of antibodies to HTLV-III.

17 Claims, 22 Drawing Sheets

Sequence of BH8-ENV    Clone G

| | | | | | | |
|---|---|---|---|---|---|---|
| 7199 | GATCTTCAGA | CCTGGAGGAG | GAGATATGAG | GGACAATTGG | AGAAGTGAAT | TATATAAATA |
| 7259 | TAAAGTAGTA | AAAATTGAAC | CATTAGGAGT | AGCACCCACC | AAGGCAAAGA | GAAGAGTGGT |
| 7319 | GCAGAGAGAA | AAAAGAGCAG | TGGGAATAGG | AGCTTTGTTC | CTTGGGTTCT | TGGGAGCAGC |
| 7379 | AGGAAGCACT | ATGGGCGCAG | CGTCAATGAC | GCTGACGGTA | CAGGCCAGAC | AATTATTGTC |
| 7439 | TGGTATAGTG | CAGCAGCAGA | ACAATTTGCT | GAGGGCTATT | GAGGGCCAAC | AGCATCTGTT |
| 7499 | GCAACTCACA | GTCTGGGGCA | TCAAGCAGCT | CCAGGCAAGA | ATCCTGGCTG | TGGAAAGATA |
| 7559 | CCTAAAGGAT | CAACAGCTCC | TGGGGATTTG | GGGTTGCTCT | GGAAAACTCA | TTTGCACCAC |
| 7619 | TGCTGTGCCT | TGGAATGCTA | GTTGGAGTAA | TAAATCTCTG | GAACAGATTT | GGAATAACAT |
| 7679 | GACCTGGATG | GAGTGGGACA | GAGAAATTAA | CAATTACACA | AGCTTAATAC | ACTCCTTAAT |
| 7739 | TGAAGAATCG | CAAAACCAGC | AAGAAAAGAA | TGAACAAGAA | TTATTGGAAT | TAGATAAATG |
| 7799 | GGCAAGTTTG | TGGAATTGGT | TTAACATAAC | AAATTGGCTG | TGGTATATAA | AATTATTCAT |
| 7859 | AATGATAGTA | GGAGGCTTGG | TAGGTTTAAG | AATAGTTTTT | GCTGTACTTT | CTATAGTGAA |
| 7919 | TAGAGTTAGG | CAGGGATATT | CACCATTATC | GTTTCAGACC | CACCTCCCAA | ACCCGAGGGG |
| 7979 | ACCCGACAGG | CCCGAAGGAA | TAGAAGAAGA | AGGTGGAGAG | AGAGACAGAG | ACAGATCCAT |
| 8039 | TCGATTAGTG | AACG | | | | | a) pJLBO
...ATGGTTCGTGCAAACAAACGCAACGAGGTCCTACGAATCGCG|GATCCG...    BamHI b) pJLBI
...ATGGTTCGT...ATCGCGG|GATCCCG...    BamHI c) pJLB2
...ATGGTTCGT...ATCGCGCG|GATACCGCG...    BamHI

RANDOM CLONING STRATEGY
BH5 or BH8
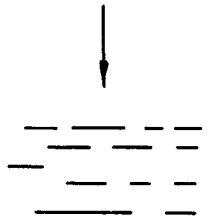
FIG. 11
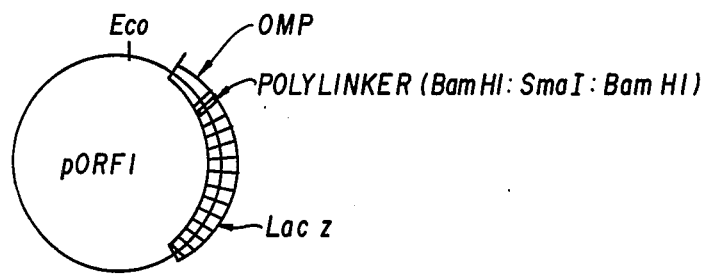

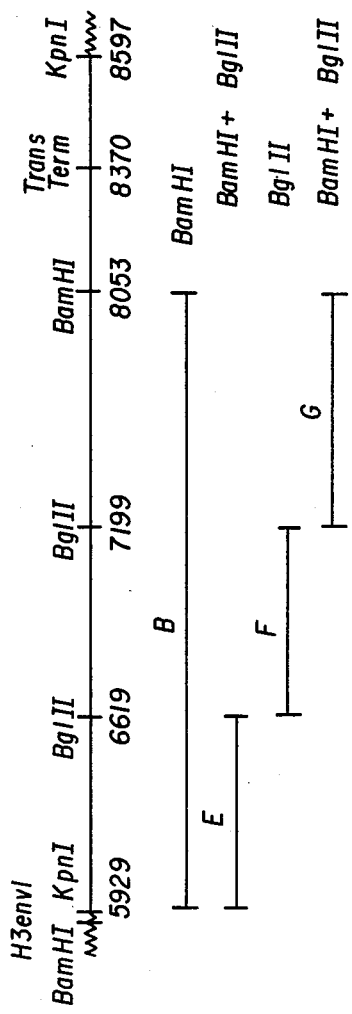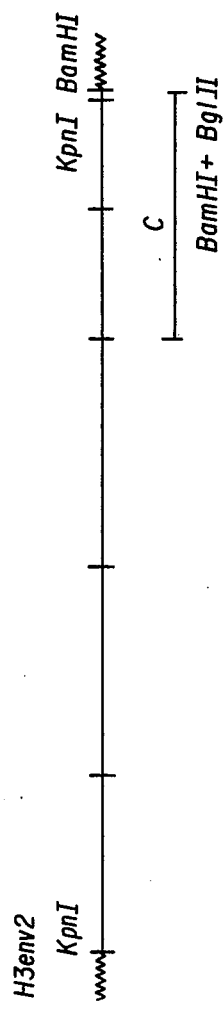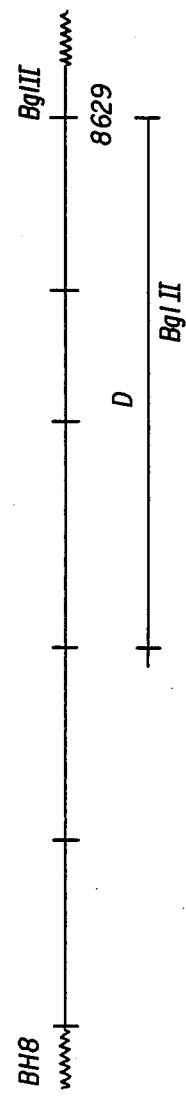
FIG.13

|  | Sequence of BH5-GAG | | | Clone Gag-1 | | |
|---|---|---|---|---|---|---|
| 653 | AGCAAAACAA | AAGTAAGAAA | AAAGCACAGC | AAGCAGCAGC | TGACACAGGA | CACAGCAGTC |
| 713 | AGGTCAGCCA | AAATTACCCT | ATAGTGCAGA | ACATCCAGGG | GCAAATGGTA | CATCAGGCCA |
| 773 | TATCACCTAG | AACTTTAAAT | GCATGGGTAA | AAGTAGTAGA | AGAGAAGGCT | TTCAGCCCAG |
| 833 | AAGTGATACC | CATGTTTTCA | GCATTATCAG | AAGGAGCCAC | CCCACAAGAT | TTAAACACCA |
| 893 | TGCTAAACAC | AGTGGGGGGA | CATCAAGCAG | CCATGCAAAT | GTTAAAAGAG | ACCATCAATG |
| 953 | AGGAAGCTGC | AGAATGGGAT | AGAGTGCATC | CAGTGCATGC | AGGGCCTATC | GCACCAGGCC |
| 1013 | AGATGAGAGA | ACCAAGGGGA | AGTGACATAG | CAGGAACTAC | TAGTACCCTT | CAGGAACAAA |
| 1073 | TAGGATGGAT | GACAAATAAT | CCACCTATCC | CAGTAGGAGA | AATTTATAAA | AGATGGATAA |
| 1133 | TCCTGGGATT | AAATAAAATA | GTAAGGATGT | ATAGTCCTAC | CAGCATTCTG | GACATAAGAC |
| 1193 | AAGGACCAAA | GGAACCCTTT | AGAGAC | | | |

| | Sequence of BH5-POL | | | Clone Pol-1 | | |
|---|---|---|---|---|---|---|
| 2600 | AGCAATATTC* | CAAAGTAGCA | TGACAAAAAT | TTTAGAGCCT | TTAGAAAAAC | AAAATCCAGA |
| 2660 | CATAGTTATT | TATCAATACA | TGGATGATTT | GTATGTAGGA | TCTGACTTAG | AAATAGGGCA |
| 2720 | GCATAGAACA | AAAATAGAGG | AGCTGAGACA | ACATCTGTTG | AGGTGGGGAT | TTACCACACC |
| 2780 | AGACAAAAAA | CATCAGAAAG | AACCTCCATT | CCTTTGGATG | GGTTATGAAC | TCCATCCTGA |
| 2840 | TAAATGGACG | ATACAGCCTA | TAGTGCTGCC | AGAAAAGAC | AGCTGGACTG | TCAATGACAT |
| 2900 | ACAGAAGTTA | GTGGGAAAAT | TGAATTGGGC | AAGTCAGATT | TATCCAGGGA | TTAAAGTAAG |
| 2960 | GCAATTATGT | AAACTCCTTA | GAGGAACCAA | AGCACTAACA | GAAGTAATAC | CACTAACAGA |
| 3020 | AGAAGCAGAG | CTAGAACTGG | CAGAAAACAG | AGAGATTCTA | AAAGAACCAG | TACATGGAGT |
| 3080 | GTATTATGAC | CCATCAAAAG | ACTTAATAGG | AGAAATACAG | AAGCAGGGGC | AAGGCCAATG |
| 3140 | GACATATCAA | ATTTATCAAG | AGCCATTTAA | AAATCTGAAA | ACAGGAAAAT | ATGCAAGAAT |
| 3200 | GAGGGGTGCC | CACACTAATG | ATGTAAAACA | ATTAACAGAG | GCAGTGCAAA | AAATAACCAC |
| 3260 | AGAAAGCATA | GTAATATGGG | GAAAGACTCC | TAAATTTAAA | CTACCCATAC | AAAAGAAAAC |
| 3320 | ATGGGAAACA | TGGTGGACAG | AGTATTGGCA | AGCCACCTGG | ATTCCTGAGT | GGGAGTTTGT |
| 3380 | TAATACCCCT | CCTTTAGTGA | AATTATGGTA | CCAGTTAGAG | AAAGAACCCA | TAGTAGGTGC |
| 3440 | AGAAACCTTC | TATGTAGATG | GGGCAGCTAG | CAGGGAGACT | AAATTAGGAA | AAGCAGGATA |
| 3500 | TGTTACTAAT | AGAGGAAGAC | AAAAAGTTGT | CACCCTAACT | CACACAACAA | ATCAGAAGAC |
| 3560 | TGAATTACAA | GCAATTCATC | TAGCTTTGCA | GGATTCGGGA | TTAGAAGTAA | ATATAGTAAC |
| 3620 | AGACTCACAA | TATGCATTAG | GAATCATTCA | AGCACAACCA | GATAAAAGTG | AATCAGAGTT |
| 3680 | AGTCAATCAA | ATAATAGAGC | AGTTAATAAA | AAAGGAAAAG | GTCTATCTGG | CATGGGTACC |
| 3740 | AGCACACAAA | GGAATTGGAG | CAAATGAACA | AGTAGATAAA | TTAGTCAGTG | CTGGAATCAG |
| 3800 | GAAAATACTA | TTTTTAGATG | GAATAGATAA | GGCCCAAGAA | GAACATGAGA | AATATCACAG |
| 3860 | TAATTGGAGA | GCAATGGCTA | GTGATTTTAA | CCTGCCACCT | GTAGTAGCAA | AA |

Sequence of BH5-POL    Clone Pol-2

| | | | | | | |
|---|---|---|---|---|---|---|
| 2743 | TGAGACAACA | TCTGTTGAGG | TGGGGATTTA | CCACACCAGA | CAAAAAACAT | CAGAAAGAAC |
| 2803 | CTCCATTCCT | TTGGATGGGT | TATGAACTCC | ATCCTGATAA | ATGGACGATA | CAGCCTATAG |
| 2863 | TGCTGCCAGA | AAAAGACAGC | TGGACTGTCA | ATGACATACA | GAAGTTAGTG | GGAAAATTGA |
| 2923 | ATTGGGCAAG | TCAGATTTAT | CCAGGGATTA | AAGTAAGGCA | ATTATGTAAA | CTCCTTAGAG |
| 2983 | GAACCAAAGC | ACTAACAGAA | GTAATACCAC | TAACAGAAGA | AGCAGAGCTA | GAACTGGCAG |
| 3043 | AAAACAGAGA | GATTCTAAAA | GAACCAGTAC | ATGGAGTGTA | TTATGACCCA | TCAAAAGACT |
| 3103 | TAATAGCAGA | AATACAGAAG | CAGGGGCAAG | GCCAATGGAC | ATATCAAATT | TATCAAGAGC |
| 3163 | CATTTAAAAA | TCTGAAAACA | GGAAAATATG | CAAGAATGAG | GGGTGCCCAC | ACTAATGATG |
| 3223 | TAAAACAATT | AACAGAGGCA | GTGCAAAAAA | TAACCACAGA | AAGCATAGTA | ATATGGGGAA |
| 3283 | AGACTCCTAA | ATTTAAACTA | CCCATACAAA | AAGAAACATG | GGAAACATGG | TGGACAGAGT |
| 3343 | ATTGGCAAGC | CACCTGGATT | CCTGAGTGGG | AGTTTGTTAA | TACCCCTCCT | TTAGTGAAAT |
| 3403 | TATGGTACCA | GTTAGAGAAA | GAACCCATAG | TAGGTGCAGA | AACCTTCTAT | GTAGATGGGG |
| 3463 | CAGCTAGCAG | GGAGACTAAA | TTAGGAAAAG | CAGGATATGT | TACTAATAGA | GGAAGACAAA |
| 3523 | AAGTTGTCAC | CCTAACTCAC | ACAACAAATC | AGAAGACTGA | ATTACAAGCA | ATTCATCTAG |
| 3583 | CTTTGCAGGA | TTCGGGATTA | GAAGTAAATA | TAGTAACAGA | CTCACAATAT | GCATTAGGAA |
| 3643 | TCATTCAAGC | ACAACCAGAT | AAAAGTGAAT | CAGAGTTAGT | CAATCAAATA | ATAGAGCAGT |
| 3703 | TAATAAAAAA | GGAAAAGGTC | TATCTGGCAT | GGGTACCAGC | ACACAAAGGA | ATTGGAGGAA |
| 3763 | ATGAACAAGT | AGATAAATTA | GTCAGTGCTG | GAATCAGGAA | AATACTATTT | TTAGATGGAA |
| 3823 | TAGATAAGGC | CCAAGAAGAA | CATGAGAAAT | ATCACAGTAA | TTGGAGAGCA | ATGGCTAGTG |
| 3883 | ATTTTAACCT | GCCACCTGTA | GTAGCAAAAG | AAATAGTAGC | CAGCTGTGAT | AAATGTCAGC |
| 3943 | TAAAAGGAGA | AGCCATGCAT | GGACAAGTAG | ACTGTAGTCC | AGGAATATGG | CAACTAGATT |
| 4003 | GTACACATTT | AGAAGGAAAA | GTTATCCTGG | TAGCAGTTCA | TGTAGCCAGT | GGATATATAG |
| 4063 | AAGCAGAAGT | TATTCCAGCA | GAAACAGGGC | AGGAAACAGC | ATATTTTCTT | TTAAAATTAG |
| 4123 | CAGGAAGATG | GCCAGTAAAA | ACAATACATA | CAGACAATGG | CAGCAATTTC | ACCAGTGCTA |
| 4183 | CGGTTAAGGC | CGCCTGTTGG | TGGGCGGGA | | | |

FIG.17

Sequence of BH8-ENV  Clone F

| | | | | | | |
|---|---|---|---|---|---|---|
| 6619 | GATCTGCCAA | TTTCACAGAC | AATGCTAAAA | CCATAATAGT | ACAGCTGGAC | ACATCTGTAG |
| 6679 | AAATTAATTG | TACAAGACCC | AACAACAATA | CAAGAAAAAA | AATCCGTATC | CAGAGGGGAC |
| 6739 | CAGGGAGAGC | ATTTGTTACA | ATAGGAAAAA | TAGGAAATAT | GAGACAAGCA | CATTGTAACA |
| 6799 | TTAGTAGAGC | AAAATGGAAT | GCCACTTTAA | AACAGATAGA | TAGCAAATTA | AGAGAACAAT |
| 6859 | TTGGAAATAA | TAAAACAATA | ATCTTTAAGC | AGTCCTCAGG | AGGGACCCA | GAAATTGTAA |
| 6919 | CGCACAGTTT | TAATTGTGGA | GGGGAATTTT | TCTACTGTAA | TTCAACACAA | CTGTTTAATA |
| 6979 | GTACTTGGnn | nnnnnnnnn | nnnAGTACTA | AAGGGTCAAA | TAACACTGAA | GGAAGTGACA |
| 7039 | CAATCACCCT | CCCATGCAGA | ATAAAACAAA | TTATAAACAT | GTGGCAGGAA | GTAGGAAAAG |
| 7099 | CAATGTATGC | CCCTCCCATC | AGTGGACAAA | TTAGATGTTC | ATCAAATATT | ACAGGGCTGC |
| 7159 | TATTAACAAG | AGATGGTGGT | AATAGCAACA | ATGAGTCCGA | | |

FIG.18

Sequence of BH8-ENV     Clone G

```
7199  GATCTTCAGA  CCTGGAGGAG  GAGATATGAG  GGACAATTGG  AGAAGTGAAT  TATATAAATA
7259  TAAAGTAGTA  AAAATTGAAC  CATTAGGAGT  AGCACCCACC  AAGGCAAAGA  GAAGAGTGGT
7319  GCAGAGAGAA  AAAAGAGCAG  TGGGAATAGG  AGCTTTGTTC  CTTGGGTTCT  TGGGAGCAGC
7379  AGGAAGCACT  ATGGGCGCAG  CGTCAATGAC  GCTGACGGTA  CAGGCCAGAC  AATTATTGTC
7439  TGGTATAGTG  CAGCAGCAGA  ACAATTTGCT  GAGGGCTATT  GAGGCCAAC   AGCATCTGTT
7499  GCAACTCACA  GTCTGGGGCA  TCAAGCAGCT  CCAGGCAAGA  ATCCTGGCTG  TGGAAAGATA
7559  CCTAAAGGAT  CAACAGCTCC  TGGGGATTTG  GGGTTGCTCT  GGAAAACTCA  TTTGCACCAC
7619  TGCTGTGCCT  TGGAATGCTA  GTTGGAGTAA  TAAATCTCTG  GAACAGATTT  GGAATAACAT
7679  GACCTGGATG  GAGTGGGACA  GAGAAATTAA  CAATTACACA  AGCTTAATAC  ACTCCTTAAT
7739  TGAAGAATCG  CAAAACCAGC  AAGAAAAGAA  TGAACAAGAA  TTATTGGAAT  TAGATAAATG
7799  GGCAAGTTTG  TGGAATTGGT  TTAACATAAC  AAATTGGCTG  TGGTATATAA  AATTATTCAT
7859  AATGATAGTA  GGAGGCTTGG  TAGGTTTAAG  AATAGTTTTT  GCTGTACTTT  CTATAGTGAA
7919  TAGAGTTAGG  CAGGGATATT  CACCATTATC  GTTTCAGACC  CACCTCCCAA  ACCCGAGGGG
7979  ACCCGACAGG  CCCGAAGGAA  TAGAAGAAGA  AGGTGGAGAG  AGAGACAGAG  ACAGATCCAT
8039  TCGATTAGTG  AACG
```

```
Ile  Glu  Pro  Leu  Gly  Val  Ala  Pro  Thr  Lys  Ala  Lys  Arg  Arg  Val  Gln  Arg  Glu  Lys
ATT  GAA  CCA  TTA  GGA  GTA  GCA  CCC  ACC  AAG  GCA  AAG  AGA  AGA  GTG  CAG  AGA  GAA  AAA gp120 | gp41
                                    bp 7349              bp 7419

Arg  Ala  Val  Gly  Ile  Gly  Gly                  Gln  Ala  Arg  Gln  Leu  Ser  Gly  Ile  Val  Gln  Gln  Gln  Asn
AGA  GCA  GTG  GGA  ATA  GGA  GGA                  CAG  GCC  AGA  CAA  TTG  TCT  GGT  ATA  GTG  CAG  CAG  CAG  AAC
                                    aa 523              aa 547

Asn  Leu  Leu  Arg  Ala  Ile  Glu  Gly  Gln  Gln  Leu  Leu  His  Leu  Gln  Leu  Val(Bal) Gln  Trp  Gly
AAT  TTG  CTG  AGG  GCT  ATT  GAG  GGC  CAA  CAG  CTG  TTG  CAT  CTG  CAA  CTC  GTC     CAG  TGG  GGC

Lys  Gln  Leu  Gln  Ala  Arg  Ile  Leu  Lys  Leu  Val  Tyr  Glu  Arg  Leu  Lys  Asp  Gln  Gln  Leu
AAG  CAG  CTC  CAG  GCA  AGA  ATC  CTG  AAA  CTG  GTG  TAC  GAA  AGA  TTG  AAG  GAT  CAA  CAG  CTC

Gly  Ile  Trp  Gly  Cys  Ser  Leu  Lys  Leu  Ile  Trp  Thr  Met  Thr  Val  Pro  Trp  Glu  Trp  Ala
GGG  ATT  TGG  GGT  TGC  TCT  CTG  AAA  CTC  ATT  TGG  ACT  ATG  ACC  GTG  CCT  TGG  GAG  TGG  GCT

Trp  Ser  Asn  Lys  Ser  Leu  Gln  Ile  Ile  Trp  Asn  Met  Asn  Asn  Trp  Met  Gln  Trp  Gln  Asp
TGG  AGT  AAT  AAA  TCT  CTG  CAG  ATT  ATT  TGG  AAC  ATG  AAT  AAC  TGG  ATG  CAA  TGG  CAG  GAC

Glu  Ile  Asn  Asn  Tyr  Thr  Leu  Ile  Leu  His  Leu  Ile  Glu  Gln  Glu  Ser  Gln  Asn  Gln  Gln
GAA  ATT  AAC  AAT  TAC  ACA  TTA  ATA  TTA  CAC  TTA  ATT  GAA  CAA  GAA  TCG  CAA  AAC  CAG  CAA

HIV Sequences
                                                                  bp 7802

Glu  Lys  Asn  Glu  Gln  Leu  Leu  Glu  Leu  Asp  Lys  Trp  Ala         Arg  Ile  Leu  Glu  Gly  Lys       ***
GAA  AAG  AAT  GAA  CAA  TTA  TTG  GAA  TTA  GAT  AAA  TGG  GCA         CGG  ATC  CTA  GAG  GGT  AAG       TAG
                                                          aa 674
                                                                   Linker and Vector
                                                                       Sequences
```

PEPTIDES FOR THE DIAGNOSIS OF HTLV-III ANTIBODIES, THEIR PREPARATION AND USE

This is a continuation-in-part of application Ser. No. 819,917 filed 11/6/88.

FIELD OF THE INVENTION

This invention is directed to the discovery that certain peptide fragments of the human T-cell leukemia (lymphotropic) virus (HTLV-III) are particularly immunoreactive to HTLV-III antibodies. These fragments can therefore be applied to immunodiagnostic tests for the detection of antibodies to HTLV-III.

BACKGROUND OF THE INVENTION

The human T-cell leukemia (lymphotropic) virus (HTLV-III) is a retrovirus which carries its genetic code on RNA. When a retrovirus infects a host cell, a DNA copy of its genome is integrated into the chromosome of its host. With some retroviruses, the DNA is integrated into the host cell's chromosomes in the form of a sequence known as a provirus. The DNA copy of the retrovirus' genetic code is synthesized by a viral enzyme called RNA dependent DNA polymerase, or reverse transcriptase. The host cells transcribe the DNA of the viral gene and synthesize the proteins encoded by the virus, which are then assembled into new viruses.

The HTLV-III RNA genome is similar to those of other retroviruses and contains at least (i) a gag gene that encodes the internal structural (nucleocapsid or core) proteins, (ii) a pol gene that encodes the reverse transcriptase, and (iii) any env gene that encodes the envelope glycoproteins of the virus. HTLV-III contains additional genes including those designated tat, sor, and 3'-ORF.

The complete DNA nucleotide sequence for HTLV-III has been reported in the literature by several researchers: Ratner et al., *Nature*, 313:277-284 (1985); Muesing et al., *Nature*, 313:450-485 (1985); Sanchez-Pescador et al, *Science*, 227:44-492 (1985); and Wain-Hopsin et al, *Cells*, 40:9-17 (1985).

Others have shown that the entire HTLV-III envelope protein can be used for diagnosis of the HTLV-III virus. Allan et al., *Science*, 228:1091-1094 (1985); Barin et al., *Science*, 228: 1094-1096 (1985); and Veronese et al., *Science*, 229: 1402-1405 (1985).

Molecular cloning of portions of the virus sequence has been achieved, as described in Ratner et al., supra; Chang et al., *Bio/Technology*, 3: 905-909 (1985); Chang et al., *Science*, 228: 93-96 (1985); and Crowl et al., *Cell*, 41: 979-986 (1985). These clones provide material for analysis of possible polypeptide epitopes on the HTLV-III viral surface against which the immune system can mount an antibody reaction. Identification of these epitopes is important in the development of sensitive and rapid methods for the diagnosis of AIDS.

SUMMARY OF THE INVENTION

Recognizing the role that epitopes on the viral surface play in immunological diagnosis, the inventors evaluated the provirus of the human T-cell leukemia virus-type III (HTLV-III) in an effort to identify diagnostic regions. These efforts have culminated in the identification of specific peptide fragments or constructs thereof which are particularly immunoreactive to anti-HTLV-III antibodies. The inventors have further modified these diagnostic peptides, increasing significantly the degree of immunoreactivity.

The inventors then successfully achieved high levels of expression of these diagnostic peptides by genetic engineering methods.

Diagnostic assays involving the use of these peptides have also been developed for the detection of antibodies to HTLV-III in samples suspected of containing antibodies against the HTLV-III virus.

BRIEF DESCRIPTION OF THE DRAWINGS

FIG. 11 shows the random cloning strategy for expressing clones.

FIG. 13 shows the restriction fragments obtained from the direct cloning strategy.

Restriction sites are numbered using the first nucleotide on the 3' side of the cleavage site.

Figure 14:
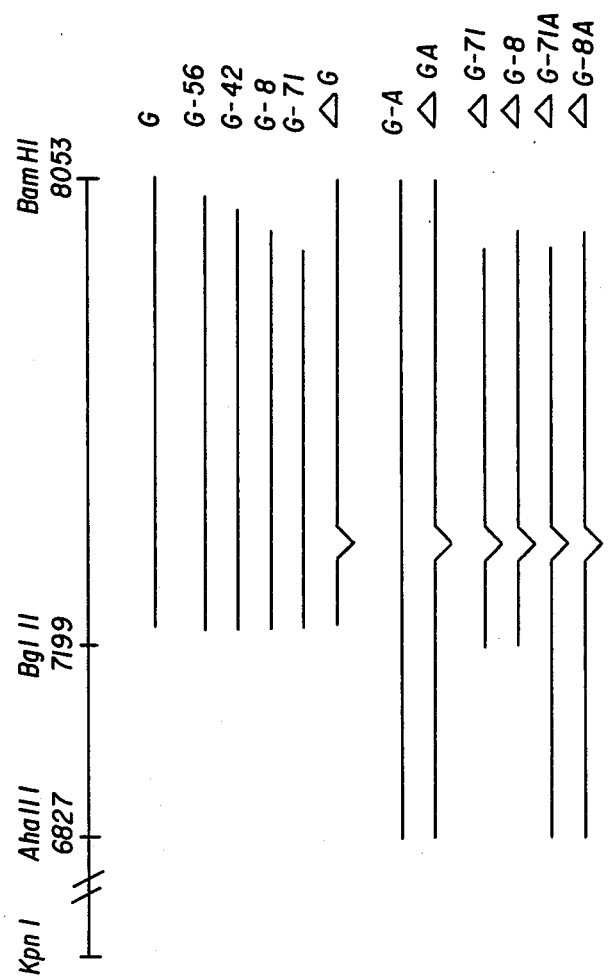

FIG. 14 shows the modifications to clone G for increased expression.

FIGS. 15-19 show five particularly immunodiagnostic regions of HTLV-III. The nucleotide sequences are respectively, FIG. 15: 653-1218; FIG. 16: 2600-3911; FIG. 17: 2743-4211; FIG. 18: 6619-7198; and FIG. 19: 7199-8052. Legend: BH10 and BH5 represent clone nomenclature; the set of numbers to the left of the sequences represent nucleotide residues.

In FIGS. 18 and 19 the * identifies the first base of the first codon entirely encoded by HTLV-III sequences. Additional codons generated by ligation of HTLV-III sequences to those in the expression vector may or may not be identical to those found in HTLV-III itself. The sequences 6987-7001 in clone F are listed as "n". These nucleotides are deleted in BH8 with respect to BH10.

The actual sequence of BH8 in this region is TTGGACTA, ie: nucleotide 6988 is followed by nucleotide 7002. The n's are included to maintain numbering that is consistent with that published by Ratner et al.

Figure 20:
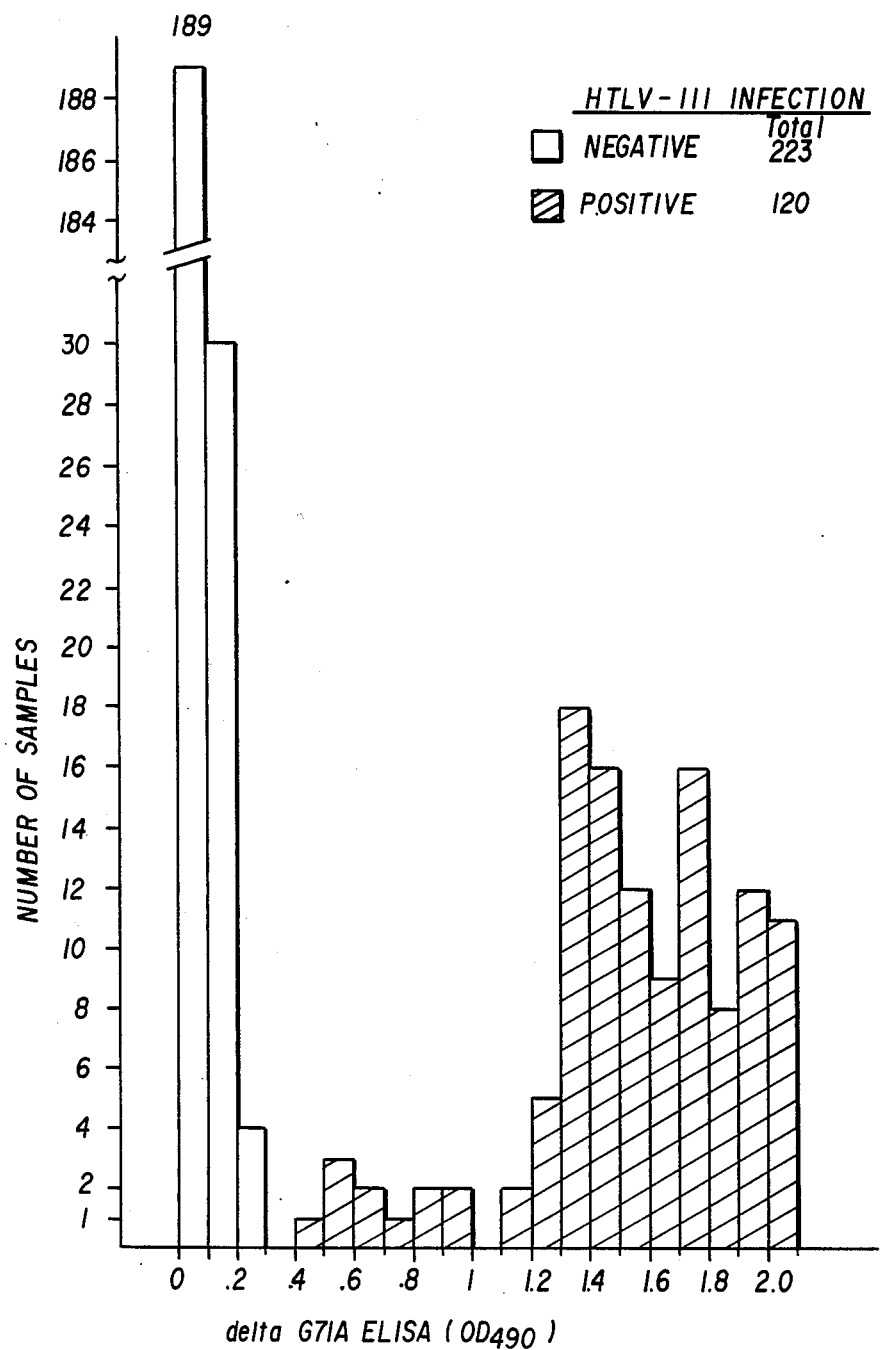

FIG. 20 shows the ELISA assay using the peptide fragment delta G-71A on both control and human patient sera.

Figure 21:
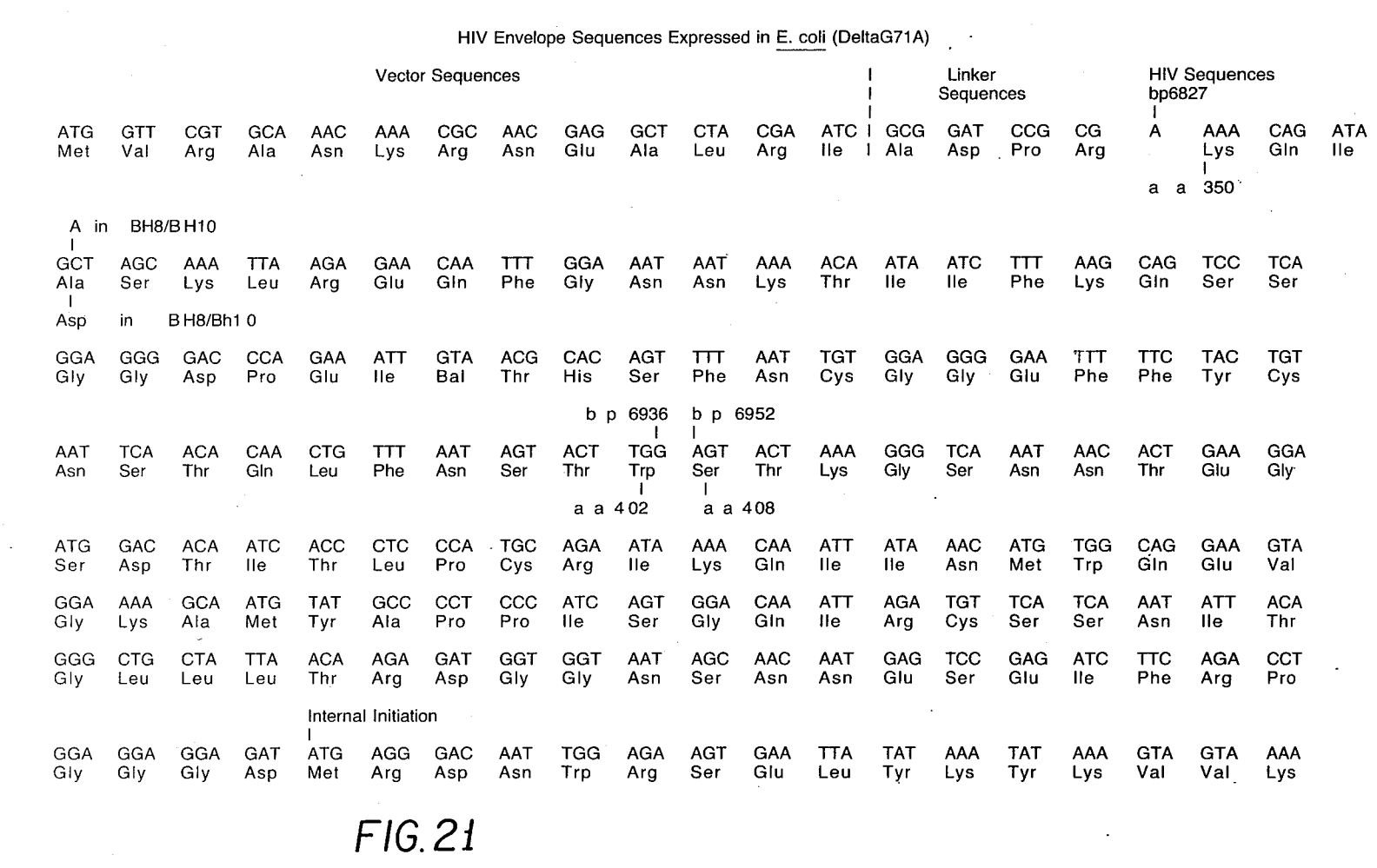

FIG. 21 shows the envelope sequences expressed in E. coli by the Delta G71A peptide fragment.

DEFINITIONS

In the description that follows, a number of terms used in recombinant DNA technology are extensively utilized. In order to provide a clearer and consistent understanding of the specification and claims, including the scope to be given such terms, the following definitions are provided.

Promoter. A DNA sequence generally described as the 5' region of a gene, located proximal to the start codon. At the promoter region, transcription of an adjacent gene(s) is initiated.

Gene. A DNA sequence that contains information for construction of a polypeptide or protein, and as used herein, includes the 5' and 3' ends.

Structural gene. A DNA sequence that is transcribed into messenger RNA that is then translated into a sequence of amino acids characteristic of a specific polypeptide. Typically the first nucleotide of the first translated codon is numbered +1, and the nucleotides are numbered consecutively with positive integers through the translated region of the structural gene and into the 3' untranslated region. The numbering of nucleotides in the promoter and regulatory region 5' to the translated region proceeds consecutively with negative integers with the 5' nucleotide next to the first translated nucleotide being numbered −1.

Operably linked. As used herein means that the promoter controls the initiation of the expression of the polypeptide encoded by the structural gene.

Expression. Expression is the process by which a structural gene produces a polypeptide. It involves transcription of the gene into messenger RNA (mRNA) and the translation of such mRNA into polypeptide(s).

Cloning vehicle. A plasmid or phage DNA or other DNA sequence which is able to replicate in a host cell, which is characterized by one or a limited number of endonuclease recognition sites at which such DNA sequences may be cut in a determinable fashion without loss of an essential biological function of the DNA, and which contain a phenotypic selection marker suitable for use in the identification of transformed cells. Markers, for example, are tetracycline resistance or ampicillin resistance. The word "vector" is sometimes used for cloning vehicle.

Expression vehicle. A vehicle similar to a cloning vehicle but which is capable of expressing a given structural gene in a host, normally under control of certain regulatory sequences. Such vehicles are designed to promote the expression of gene inserts. Typically, a restriction fragment carrying the regulatory sequences of a gene is ligated in vitro to a plasmid containing a restriction fragment possessing the gene but lacking its regulatory sequences. The plasmid with this new combination of DNA sequences is then cloned under circumstances that promote the expression of the gene under the control of the regulatory sequences.

Host. Any organism that is the recipient of a replicable expression vehicle.

DESCRIPTION OF THE PREFERRED EMBODIMENTS

The complete DNA nucleotide sequence and the predicted amino acid sequence for the HTLV-III provirus from the H9/HTLV-III cell line is described in Ratner, et al., Nature, 313: 277–284 (1985) herein incorporated by reference. Clones BH5 and BH8, isolated from cell line H9, constituted the starting material of the invention herein described. The H9/HTLV-III cell line is deposited in the American Type Culture Collection under ATCC No. CRL 8543 and generally described in U.S. Pat. No. 4,520,113. The HTLV-III virus can also be propagated using lysates of immortalized human T-cell clones.

Various nucleotide sequences encoding peptide fragments of the BH5 and BH8 clones were evaluated to determine immunodiagnostic regions. The particular peptide fragments of the HTLV-III provirus discovered by the inventors to be particularly immunoreactive, and therefore immunodiagnostic for AIDS antibodies, are encoded for (or present within) the nucleotide sequences 653–1218, 2600–3911, 2743–4211, 6619–7198, and 7199–8052 as that sequence is numbered in FIG. 1 of Ratner et al., supra. These five regions are shown in FIGS. 15–19 of the present application. As used herein and where appropriate, the nucleotide sequence numbering is based on the first nucleotide beginning on the 3' side of the restriction endonuclease clip site.

The preferred peptide fragments are those encoded for (or present within) the nucleotide sequences 2600–3911, 2743–4211, and 7199–8052. The most preferred peptide fragment is (or is within) 7199–8052.

Additionally, the inventors have discovered that deleting the DNA sequence encoding certain hydrophobic region(s) of the fragments results in increased expression of the fragment, and also in a high degree of immunoreactivity to HTLV-III antibodies. The hydrophobic regions are those regions comprising hydrophobic amino acids encoded for by various nucleotide segments of the HTLV-III virus. In a preferred embodiment, two hydrophobic regions of the immunogenic peptide fragment encoded for by the nucleotide sequences 7199–8052 have been deleted. These two hydrophobic regions are encoded approximately between nucleotides 7352 and 7418 and approximately between nucleotides 7851 and 7916.

Moreover, the inventors have also discovered that extending the amino end of a peptide fragment having the hydrophobic region deleted results in increased expression of the fragment and in a high degree of immunoreactivity to HTLV-III antibodies. Thus, in another preferred embodiment, the amino end of the hydrophobic double-deleted peptide fragment encoded for by nucleotide sequences 7199–8052 is extended. In the most preferred embodiment, the amino end of the hydrophobic double-deleted peptide fragment encoded for by nucleotide sequences 7199–8052 is extended to the Aha III site, at about nucleotide 6827. This portion of the HTLV-III, nucleotides 6827 to 8052, contains nearly all of the conserved envelope sequences among HTLV-III isolates known to date. This particular peptide fragment has been designated delta G-71A and an *E. coli* culture (MZ1) containing a plasmid that expresses this peptide has been designated p-delta-G71AC. This culture was deposited in American Type Culture Collection, 12301 Parklawn Dr., Rockville, Md. 20852, under ATCC No. 53455 on Jan. 30, 1986. This depository assures permanence of the deposit and ready accessibility thereto by the public.

As will be understood by one of skill in the art, there may be variations in the first one or two amino acids of the peptide fragments due to proper alignment of the cloned nucleotide sequence in the expression vehicle. The nucleotide sequence of mRNA is translated in groups of three nucleotides, called codons. Each codon is represented by a single amino acid in the peptide fragment synthesized. The reading-frame defines which sets of three nucleotides are read as codons, determined by the initiation codon AUG.

Of particular interest are peptides of the following formula:

(1) $H_2N-X-CO-R^1$ wherein $R^1$ is $Cys-CO-R^2$, OH, OM or $-NR^3R^4$;
  M is a pharmaceutically acceptable cation or a lower ($C_1$-$C_6$) branched or unbranched alkyl group;
  $R^2$, $R^3$ and $R^4$ are the same or different and selected from the group consisting of hydrogen and a lower ($C_1$-$C_6$) branched or unbranched alkyl group; and
  X is the amino acid sequence or peptide fragment as described above;
(2) the acid addition salts thereof; and
(3) the protected or partially protected derivatives thereof.

As is known in the art, the amino acid residues may be in their protected or unprotected form, using appropriate amino or carboxyl protecting groups.

Useful cations M are alkali or alkaline earth metallic cations (i.e., Na, K, Li, ½Ca, ½Ba, etc.) or amine cations (i.e., tetraalkylammonium, trialkylammonium, where alkyl can be $C_1$-$C_{12}$).

The variable length peptides may be in the form of the free amines (on the N-terminus), or acid-addition salts thereof. Common acid addition salts are hydrohalic acid salts, i.e., HBr, HI, or more preferably, HCl.

The peptide fragments of the HTLV-III virus may be obtained from the provirus in a host cell. The peptide fragment would then be obtained by fragmenting the naturally-occurring virus using suitable enzymes or chemical methods. However, it is possible to obtain the peptide fragments by synthesis, for example, by well known solid phase peptide synthesis described in Merrifield, J. Am. Chem. Soc., 85: 2149 (1962) and Stewart and Young in *Solid Phase Peptide Synthesis* (Freeman, San Francisco 1969) at 27–62.

A preferred method of obtaining the peptide fragment is by cloning the desired polynucleotide fragment utilizing genetic engineering techniques. The advantages of using genetic engineering and recombinant clones are twofold: the first advantage is that it is difficult and time-consuming to obtain large amounts of the viral genome either by isolation techniques or by synthesis; the second advantage is that recombinant peptides are devoid of human antigens that may reduce the reliability of a diagnostic test.

The term "peptide fragment," is thus meant to include naturally-occurring amino acid sequences, synthetic sequences, and expressed fragments from cloned sequences representing segments of the HTLV-III viral genome.

It will be understood by one of skill in the art that there may be some variation in the diagnostic peptide fragments, as described above, provided however, that these peptides retain immunoreactivity to antibodies to the HTLV-III virus. Thus, the ranges in the length of the peptide fragments need not be precisely fixed. Amino acids of the peptide fragments may be deleted or added without loss of immunoreactivity. Additionally, amino acids could be exchanged, e.g. a neutral amino acid such a valine could be exchanged with another neutral amino acid, such as leucine. There is also genomic variation from isolate to isolate. (See, for example, Wong-Staal et al., Science, 229: 759–762 (1985)). It is to be understood that such variations are included in the peptide fragments of this invention.

The genetic constructs and the methods for using them can be utilized for expression of the peptide fragments in hosts, including procaryotic and eucaryotic hosts. The procaryotic hosts may include bacteria, such as *E. coli* and *S. typhimurium, Serratia marcescens,* or *Bacillus subtilis.* The preferred bacterial host for expression is an *E. coli* strain that contains a temperature sensitive bacteriophage lamda CI857 gene, such as MZ1, described in Lautenberger et al., *Gene Anal. Tech,* 1: 63–66 (1984). Eucaryotic hosts may include yeast, filamentous fungi, and mammalian cells. The DNA sequence of the peptide fragments can be inserted into the genome for vaccinia virus. (Mackett, M. *et al., Proc. Natl. Acad. Sci.* USA, 79: 7415 (1982); Panicali, D. et al., Proc. Natl. *Acad. Sci. USA,* 79: 4927 (1982); Panicali, D. et al., *Proc. Natl. Acad. Sci.* USA, 80: 5364 (1983); and Smith, G. L. et al., *Nature,* 302: 490 (1983).) The recombinant vaccinia virus then replicates in any mammalian cell and the fragment of interest appears on the envelope or in internal viral proteins. Insect cells can also be used for replication of the fragments. (See, for example, Smith et al., *Molecular and Cell Biology,* 3: 2156–2165 (1983)).

In general, expression vectors containing promoter sequences which facilitate the efficient transcription of the inserted gene fragment, which are derived from species compatible with the host cells, are used in connection with these hosts. The expression vector typically contains an origin of replication, promoters, terminators, as well as specific genes which are capable of providing phenotypic selection in transformed cells.

The transformed host cell can be fermented and cultured according to means known in the art to achieve optimal cell growth, and also to achieve optimal expression of the cloned HTLV-III peptide fragments. As described hereinbelow in Example 5, high level expression of the cloned HTLV-III virus sequences coding for peptide fragments can be achieved according to a preferred procedure of this invention.

After expression of the cloned HTLV-III peptide fragments, the fragments will typically be recovered and purified according to means known in the art. When bacteria is used as the host, high-level expression the clones usually results in the formation of insoluble inclusion bodies or aggregates. To purify the expressed clones, the insoluble inclusion bodies must be made soluble. In the preferred embodiment of this invention, the expressed peptide fragments are purified in a process using citraconylation, as that process is more fully described in Example 8.

The purified immunogenic and diagnostic peptide fragments according to this invention are specifically recognized by antibodies produced in response to the HTLV-III virus. The HTLV-III antibodies in blood or tissue samples can be detected using the peptide fragments in immunoassays wherein the peptides can be utilized in liquid phase or bound to a solid phase carrier. In addition, the peptide fragments can be detectably labeled in various ways for use in immunoassays for virus. The preferred immunoassays for detecting HTLV-III antibodies using the peptide fragments of this invention include radioimmunoassays, enzyme-linked immunosorbent assays, (ELISA), or other assays known in the art, such as immunofluorescent assays, chemiluminescent assays, or bioluminescent assays.

Radioactive isotopes which are particularly useful in assays are $^3H$, $^{125}I$, $^{131}I$, $^{32}P$, $^{35}S$, $^{14}C$, $^{51}Cr$, $^{36}Cl$, $^{57}Co$, $^{58}Co$, $^{59}Fe$, $^{75}Se$, and $^{152}Eu$.

While radiolabeling represents one embodiment, alternatively, the peptide sequence or antibodies thereto may also be labeled using fluorescent labels, enzyme labels, free radical labels, avidin-biotin labels, or bacteriophage labels, using techniques known to the art (Chard, *Laboratory Techniques in Biology,* "An Introduction to Radioimmunoassay and Related Techniques," North Holland Publishing Company (1978).

Typical fluorescent labels include fluorescein isothiocyanate, rhodamine, phycoerythrin, phycocyanin, allophycocyanin, o-phthaldehyde, and fluorescamine.

Typical chemiluminescent compounds include luminol, isoluminol, aromatic acridinium esters, imidazoles, acridinium salts, and the oxalate esters. Typical bioluminescent compounds include luciferin, luciferase, and aequorin.

Typical enzymes include alkaline phosphatase, beta-galactosidase, glucose-6-phosphate dehydrogenase, maleate dehydrogenase, glucose oxidase, and peroxidase.

Two principal types of enzyme assays are enzyme-linked immunosorbent assay (ELISA) and the homogeneous enzyme immunoassay, also known as enzyme-multiplied immunoassay (EMIT) (Syva Corp.). The EMIT system depends on deactivation of the enzyme in the tracer-antibody complex; the activity can thus be measured without the need for a separation step.

The immunoassays within the scope of the present invention include both immunometric assays and competitive assays.

Immunometric assays include forward sandwich, reverse sandwich immunoassays and simultaneous assay. Each of these terms is well understood by those skilled in the art. The immunometric assays will be described for the detection of antibodies to the HTLV-III. In these assays, the peptide fragment is bound to the solid phase carrier and anti-IgG antibodies are detectably labeled.

In a forward sandwich immunoassay, a sample suspected of containing antibodies against HTLV-III is first incubated with a solid phase immunoabsorbent containing the peptide fragment. Incubation is continued for a period of time sufficient to allow the antibodies in the sample to bind to the immobilized peptide fragment. After the first incubation, the solid phase immunoabsorbent is separated from the incubation mixture and washed to remove interfering substances which also may be present in the sample. Solid phase immunoabsorbent-containing antibodies bound to the immobilized peptide fragments is subsequently incubated for a second time with soluble labeled antibody cross-reactive with a different domain on the antibody to be detected. After the second incubation, another wash is performed to remove unbound labeled antibody from the solid phase immunoabsorbent and to remove non-specifically bound labeled antibody. Labeled antibody bound to the solid phase immunoabsorbent is then detected and the amount of labeled antibody detected serves as a direct measure of the amount of antibodies present in the original sample. Alternatively, labeled antibody which is not associated with the immunoabsorbent complex can also be detected, in which case the measure is in inverse proportion to the amount of antigen present in the sample. Forward sandwich assays are described, for example, in U.S. Pat. Nos. 3,867,517; 4,012,294; and 4,376,110.

In a reverse sandwich assay, the sample suspected of containing test antibodies against HTLV-III is initially incubated with labeled anti-antibody, after which the solid phase immunoabsorbent containing immobilized peptide fragment cross-reactive with a different domain on the test antibody is added thereto, and a second incubation is carried out. The initial washing step required by a forward sandwich assay is not required, although a wash is performed after the second incubation. Reverse sandwich assays have been described, for example, in U.S. Pat. Nos. 4,098,876 and 4,376,110.

In a simultaneous sandwich assay, the sample, the immunoabsorbent having immobilized peptide fragment thereon and labeled soluble antibody specific to a different domain of the test antibody are incubated simultaneously in one incubation step. The simultaneous assay requires only a single incubation and does not require washing steps. The use of a simultaneous assay is a very useful technique, providing ease of handling, homogeneity, reproducibility, linearity of the assays, and high precision. See U.S. Pat. No. 4,376,110 to David et al., incorporated by reference herein.

So-called delayed immunometric assays can also be utilized, as are, for example, described in Chu, U.S. Pat. No. 4,289,747, and Wolters, U.S. Pat. No. 4,343,896.

In each of the above assays, the sample-containing antibody, solid phase immunoabsorbent with immobilized peptide fragment and labeled soluble antibody are incubated under conditions and for a period of time sufficient to allow the test antibodies to bind to the immobilized peptide fragments and to the soluble antibodies. In general, it is desirable to provide incubation conditions sufficient to bind as much antibody as possible, since this maximizes the binding of labeled antibody to the solid phase, thereby increasing the signal. Of course, the specific concentrations of labeled antibodies and immobilized fragments, the temperature and time of incubation, as well as other such assay conditions, can be varied, depending upon various factors including the concentration of antibody in the sample, the nature of the sample, and the like. Those skilled in the art will be able to determine operative and optimal assay conditions for each determination by employing routine experimentation.

There are many solid phase immunoabsorbents which have been employed and which can be used in the present invention. Well known immunoabsorbents include beads formed from glass, polystyrene, paper, polypropylene, dextran, nylon, and other material; tubes formed from or coated with such materials, and the like. The immobilized peptide fragments may be covalently or physically bound to the solid phase immunoabsorbent, by techniques such as covalent bonding via an amide or ester linkage or by absorption. Those skilled in the art will know many other suitable carriers for binding peptide fragments, or will be able to ascertain such, using routine experimentation.

General competitive binding assay techniques useful for the detection of minute amounts of organic molecules such as hormones, proteins, antibodies, and the like are well known in the art. See Chard, supra. Any of these competitive binding assay techniques can be used for the purposes of detecting HTLV-III antibodies. In order to carry out a competitive binding assay, typically a radio-immunoassay (RIA), it is necessary to provide a binding molecule which has affinity for the label-containing antibody raised in response to a peptide fragment, and for the HTLV-III antibody to be tested as well. A small amount of the fluid or tissue sample containing an unknown quantity of HTLV-III antibody is incubated in the presence of the raised labelled antibody and also a known amount of antibody-specific peptide fragment.

An agglutination assay can also be used to detect HTLV-III antibodies. For example, the desired fragment is immobilized on a suitable particle, for example, latex, gelatin, red blood cells, nylon, liposomes, gold particles, etc. The presence of antibodies in the sample causes agglutination, similar to that of a precipitation reaction, which can then be detected by such techniques as nephelometry, turbidity, infrared spectrometry, visual inspection, colorimetry, and the like.

The raised antibody is preferably generated with antigenic peptide fragments of the invention. Once the incubation of the test sample with the fragment and tracer-containing antibody is complete, it is necessary to determine the distribution of the tracer-containing molecule between the free and bound (immunocomplexed) form. Usually, but not always, this requires that the bound fraction be physically separated from the free fraction. For example, the specific peptide fragment can be bound to a plate. A variety of other techniques may be used for that purpose, each exploiting physical-chemical differences between the tracer-containing molecule in its free and bound form. The generally available methodologies have been described by Yalow, in Pharmacol. Rev., 28: 161 (1973). These techniques include adsorption, precipitation, salting out techniques, organic solvents, electrophoretic separation, and the like. See Chard, supra, pp. 405–422.

As in the immunometric assays described above, the soluble antibody may be labeled with any detectable label, such as a radiolabel, a fluorescent label, and enzyme lable, a free radical label, or a bacteriophage lable. Most commonly, the label, is a radiolabel or an enzyme label.

The immunogenic peptide fragments according to this invention may be used to stimulate the production of antibodies. In order to stimulate the production of antibody, the peptide fragment may be coupled to a carrier protein such as bovine serum albumin or keyhole limpet hemocyanin (KLH), utilizing techniques well known and commonly used in the art. Preferably, the carrier protein is KLH, linked to the peptide fragment through a cysteine residue.

Additionally, the peptide fragments can be admixed with an immunologically inert or active carrier. Carriers which promote or induce immune responses, such as Freund's complete adjuvant, can be utilized.

The preparation of antisera in animals is a well known technique (see, for example, Chard, supra, pages 385–396). The choice of animal is usually determined by a balance between the facilities available, and the likely requirements in terms of volume of the resultant antiserum. A large species such as goat, donkey and horse may be preferred, because of the larger volumes of serum readily obtained. However, it is also possible to use smaller species such as rabbit or guinea pig which often yield high titer antisera. Usually, subcutaneous injection of the antigenic material (the peptide fragment hapten-carrier protein conjugate) are introduced into the immune system of the animal in which antibodies are to be raised. The detection of appropriate antibodies may be carried out by testing the antisera with appropriately labeled tracer-containing molecules. Fractions that bind tracer-containing molecules are then isolated and further purified if necessary.

Antibodies thus obtained may then be utilized in various immunoassays to identify and quantitate the HTLV-III virus or fragments thereof. Both polyclonal antibodies and monoclonal antibodies, produced by well known techniques as described in Kohler and Milstein, Nature, 256: 496 (1975), raised in response to the peptide fragments of this invention can be utilized in immunoassays.

When one uses immunometric assays to detect the HTLV-III virus or portions thereof two separate and distinct antibodies are required. One of these antibodies is bound to the solid phase support while the other is detectably labeled. In essence, the two different antibodies, although specific for HTLV-III virus, are cross-reactive with different domains on viral protein. In one embodiment, the two different antibodies may be prepared by using two different peptide fragments according to this invention. The use of antibodies to different peptide fragments, one bound to a carrier and the other detectably labeled, is useful in various sandwich assays.

Alternatively, it is also possible to prepare antibodies which are specific to the HTLV-III virus, but cross-reactive with different domains by producing the antisera in two different species, for example, in rabbit and in mouse, utilizing the same peptide fragment.

In addition, the materials for use in the assays of the invention are ideally suited for preparation of a kit. Such a kit may comprise a carrier means being compartmentalized to receive in close confinement one or more container means such as vials, test tubes, and the like. Each of said container means comprises one of the separate elements to be used in the method.

For example, one of said container means may comprise immunoabsorbent-bound peptide fragment. Such fragment may be bound to a separate solid phase immunoabsorbent or directly to the inner walls of a container. A second container may comprise detectably labeled anti-antibody in lyophilized form or in solution.

The carrier may also contain, in addition, a plurality of containers each of which comprises different, predetermined known amounts of antibody. These latter containers can then be used to prepare a standard curve from which can be interpolated the results obtained from the sample containing the unknown amount of antibody.

For purposes of the invention, HTLV-III antibody or the virus itself or portions thereof may be present in biological fluids and tissues. Any sample containing the unknown amount of HTLV-III antibodies or HTLV-III can be used. Normally, a sample is a liquid such as, for example, urine, saliva, tear drops, cerebrospinal fluid, blood, serum and the like, or a solid or semi-solid such as, for example, tissues, feces, and the like. As is known in the art, the HTLV-III virus and antibodies to the virus are associated with the T-cell disorder, Acquired Immune Deficiency Syndrome (AIDS) and pre-AIDS conditions, such as AIDS-related complex (ARC). In addition, it is also known in the art that antibodies to HTLV-III may be present in a human's or animal's biological fluids or tissue, without such human or animal suffering from AIDS or ARC.

The peptide fragments according to this invention may also be used as a vaccine against the HTLV-III virus. The peptide fragment may be prepared, as is generally known in the art, to stimulate the production of antibodies. Preferably, the vaccinia virus can be used according to known means for the preparation of HTLV-III vaccines.

The following examples further describe the materials and methods used in carrying out the invention. The examples are not intended to limit the invention in any manner.

EXAMPLES

For the following Examples, the following human sera was used in evaluating the immunoreactivity of the recombinant peptide fragments. Sera were obtained from clinically diagnosed AIDS or AIDS-related complex patients or controls. Each serum was tested under code for HTLV-III/LAV gp 160/120 antibody (L. W. Kitchen et al, Nature, 312: 367–369 (1984)). gp 160/120 antibody was detected in sera from every AIDS patient, but not in any sera from controls. Controls were mostly low risk individuals without clinical signs of AIDS. They included males and females, individuals from Southern, Eastern, and Western U.S. cities and Haiti; rheumatoid factor positive persons; nuclear antibody (ANA) positive people, multiparous women; and a variety of cancer patients. AIDS patients were predominantly homosexuals but also included a few women and children and some transfusion associated cases. The AIDS patients had the same geographical distribution as the controls.

EXAMPLE 1

Plasmid Preparation

Preparation of Plasmids pJLB0, pJLB1, and pJLB2 from pJLA16

Figure 1:
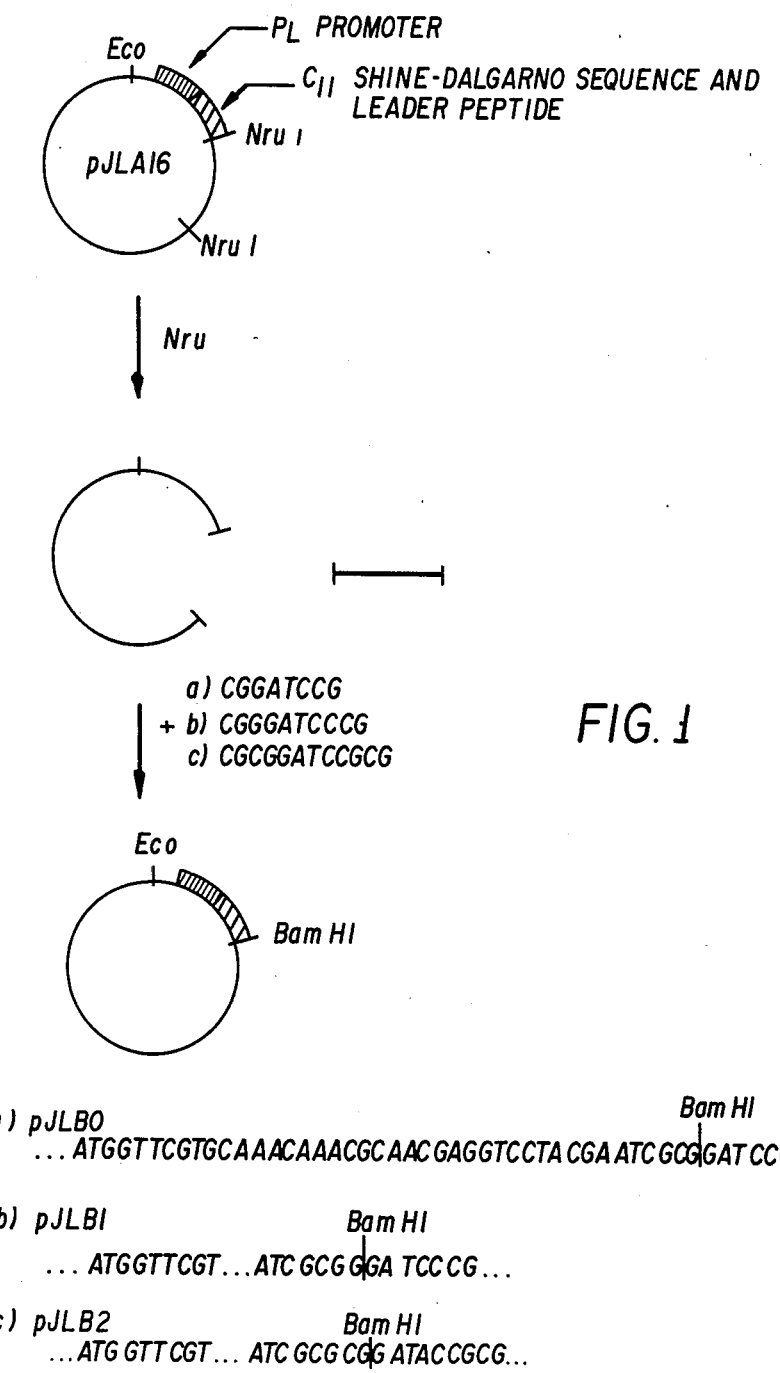
FIG. 1 shows the preparation of the plasmids pJLB0, pJLB1, and pJLB2 from pJLA16.

FIG. 1 shows the preparation of the plasmids pJLB0, pJLB1, and pJLB2 from the plasmid pJLA16. The construction of the plasmid pJLA16 is described in Lautenberger et al, Gene Anal. Tech., 1:63–66 (1984). The pJLA16 plasmid contains the bacteriophage lambda $P_L$ promoter ($P_L$), and both the Shine Dalgarno sequence and leader peptide from the bacteriophage lambda $C_{II}$ gene. The three expression plasmid vectors, pJLB0, pJLB1, and pJLB2 were prepared by digestion of pJLA16 with the restriction endonuclease NruI. After digestion, three BamHI linkers of varying lengths were ligated to the cut plasmid. This process places one BamHI restriction site at the end of the $C_{II}$ bacterial leaders in each of the translation reading frames.

Preparation of Plasmids with Translation Terminators

Figure 2:
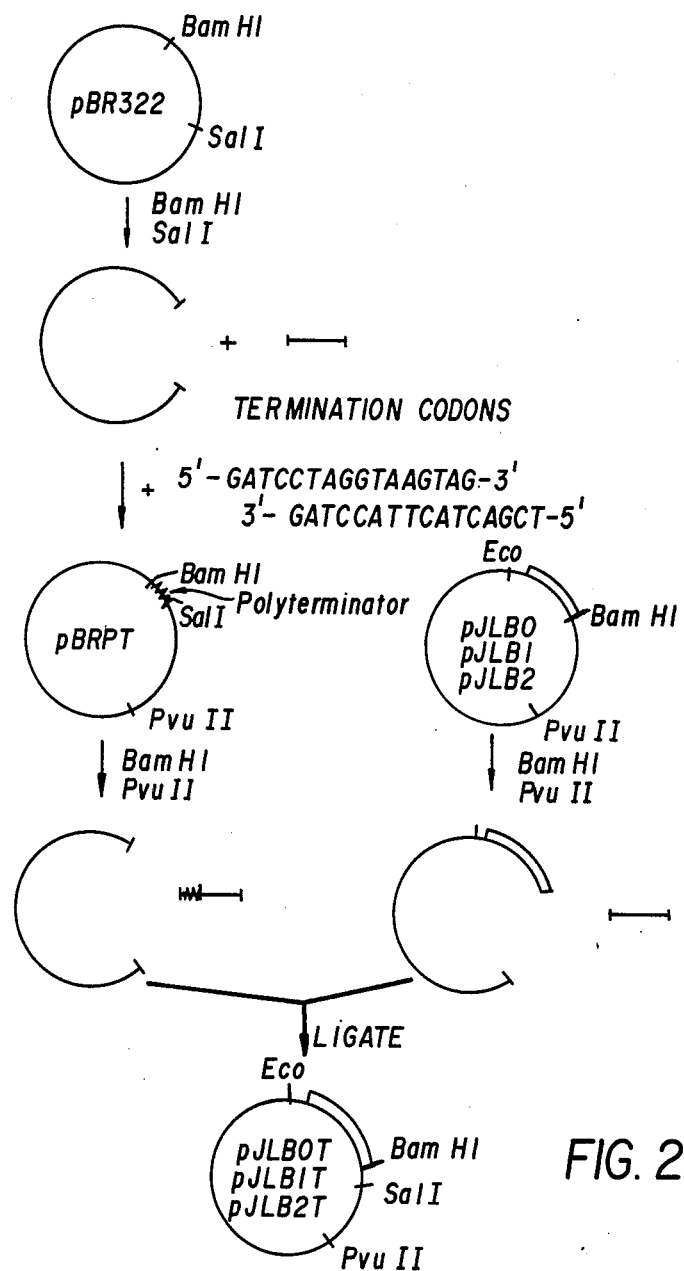
FIG. 2 shows the construction of the addition of translation polyterminator to the plasmids of FIG. 1, and the resulting plasmids pJLB0T, pJLB1T, and pJLB2T.

Referring to FIG. 2, a synthetic oligonucleotide, containing translation terminators in all three reading frames, was cloned initially into plasmid pBR322 and then shuttled into the three expresion vectors behind the BamHI cloning site. The resulting plasmids were designated pJLB0T, pJLB1T, and pJLB2T.

Preparation of Plasmids to Remove a Repressor of Transcription

Figure 3:
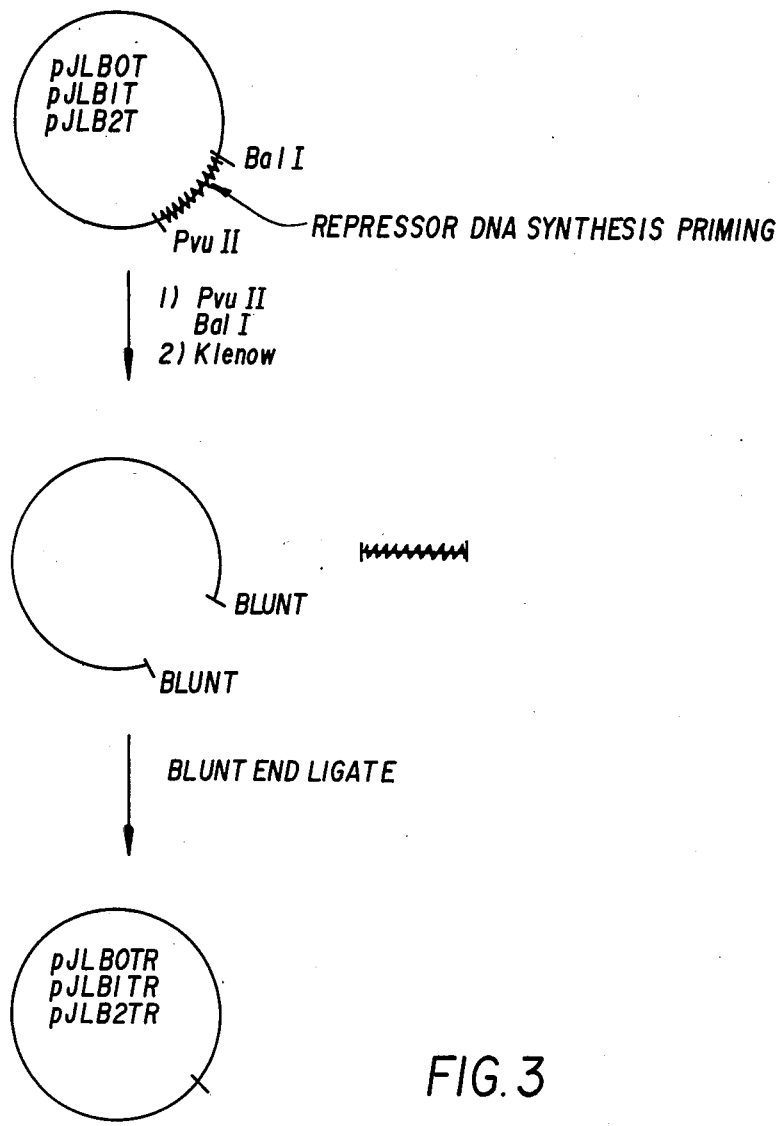
FIG. 3 shows the removal of the repressor of transcription required for priming of DNA synthesis from the plasmids of FIG. 2, and the resulting plasmids pJLB0TR, pJLB1TR, and pJLB2TR.

FIG. 3 shows removal of the portion of the plasmid vector that encodes a repressor of transcription required for priming of DNA synthesis. The plasmids, pJLB0T, pJLB1T, and pJLB2T, were digested with the restriction endonucleases PvuII and BalI and blunt ended with Klenow fragment. The blunt ends were ligated, and the resulting plasmids were designated pJLB0TR, pJLB1TR, and pJLB2TR.

EXAMPLE 2

Construction of Intermediate Clones for pL-CII Expression System

The following described plasmid series pLCBC0 and pLCBC00 were constructed in a manner similar to that for pJLA16. These constructions are described in Shimartake, H. et al., Nature, 292:128 (1981); Oppenheim, A. B. et al., J. Mol. Biol., 158:327 (1982); Lautenberger, J. A. et al., Gene, 23:75 (1983); and Lautenberger, J. A. et al., Gene Anal. Tech., 1:63 (1984).

Figure 4:
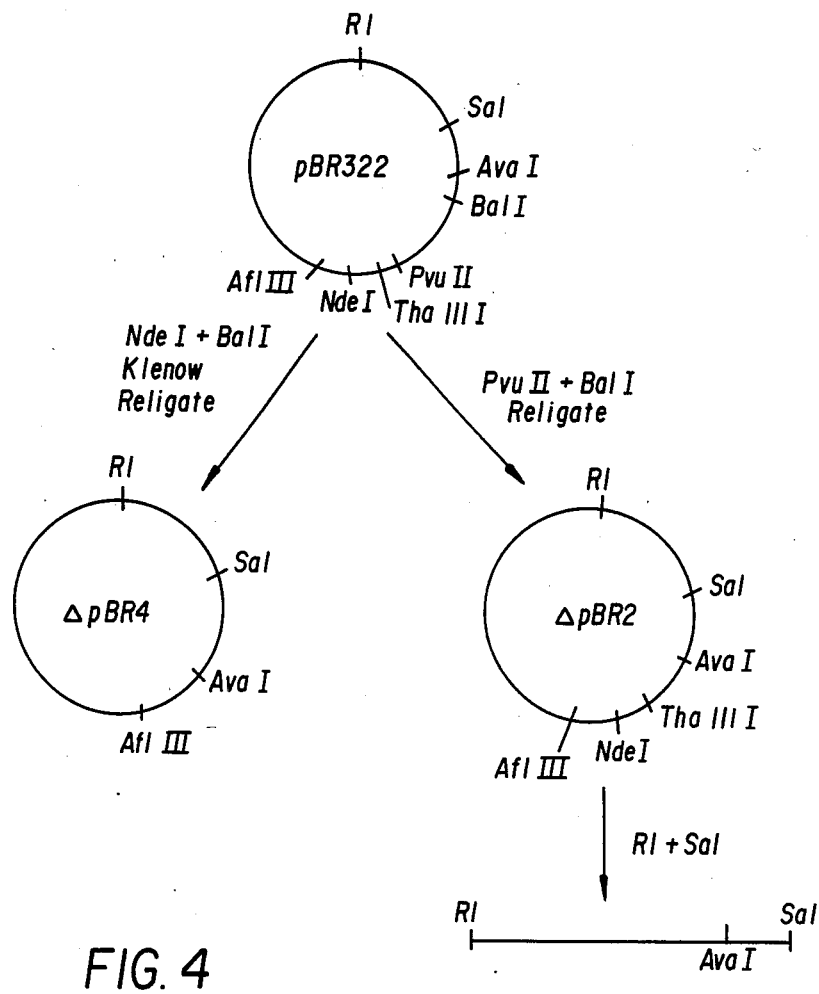
FIG. 4 shows the construction of intermediate plasmids delta pBR2 and delta pBR4 from pBR322.

FIG. 4 shows the construction of plasmids delta pBR2 and delta pBR4 from pBR322. In plasmid delta pBR2, the repressor of initiation of DNA synthesis is removed by digesting pBR322 with restriction endonucleases PvuII and BalII, then religating the plasmid. Plasmid delta pBR4 was constructed by removing the Nde I site from pBR322 by digestion with restriction endonucleases Nde I and Bal I and the ends blunt ended with Klenow fragment. The blunt ends were ligated and the resulting plasmid designated delta pBR4.

Figure 5:
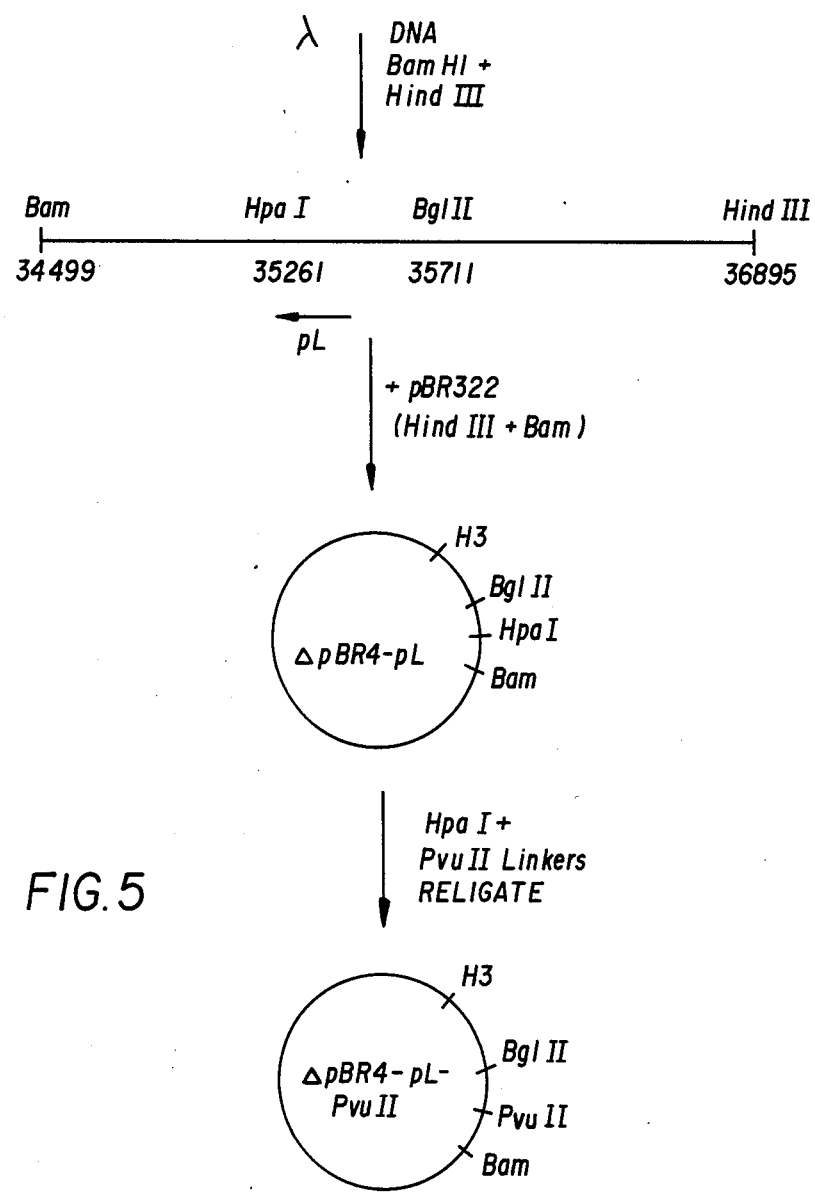
FIG. 5 shows the construction of the subcloning of the lambda pL fragment into the plasmid delta pBR4.

FIG. 5 shows the construction of the subcloning of the lambda pL fragment into the delta pBR4 plasmid, and the resulting plasmid delta pBR4-pL. The Hpa I site of delta pBR4-pL was converted to a Pvu II site, by digestion with restriction endonuclease Hpa I and ligating the plasmid with Pvu II linkers.

Figure 6:
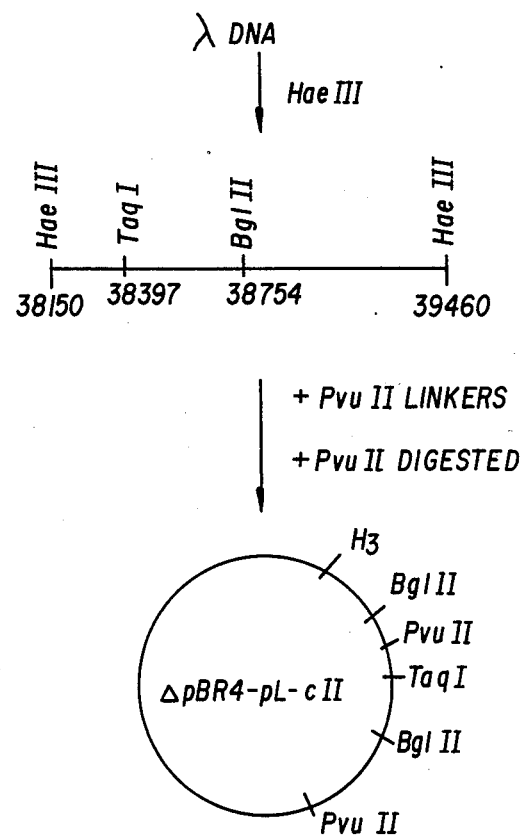
FIG. 6 shows the construction of the subcloning of the lambda cII Shine-Dalgarno sequencing behind the lambda pL promoter resulting in plasmid designated delta pBR4-pL-cII.
Figure 7:
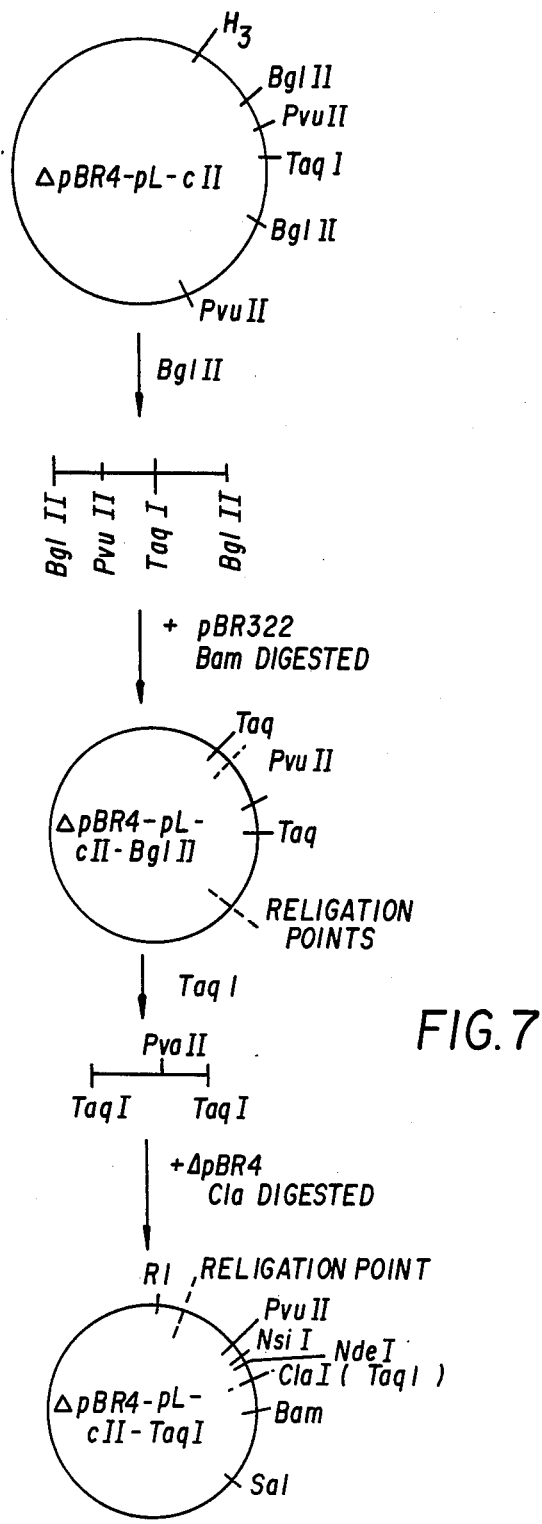
FIG. 7 shows the two step subcloning of the Taq 1 fragments into plasmid delta pBR4-pL-cII, and the resulting plasmid denoted plasmid delta pBR4-pL-cII-Taq I.
Figure 8:
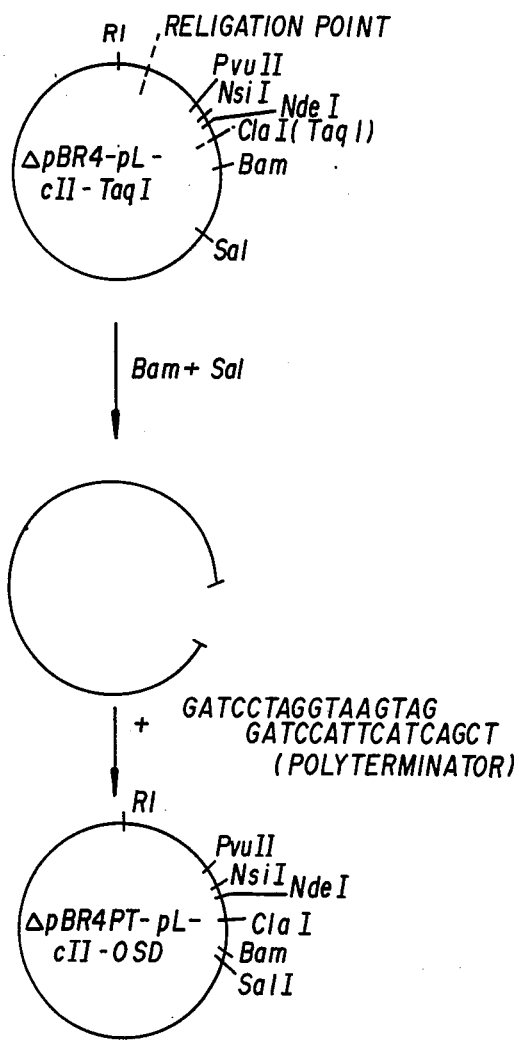
FIG. 8 shows the construction of the addition of translation polyterminator to plasmid delta pBR4-pL-cII-Taq I, and the resulting plasmid delta pBRPT-pL-cII-OSD.
Figure 9:
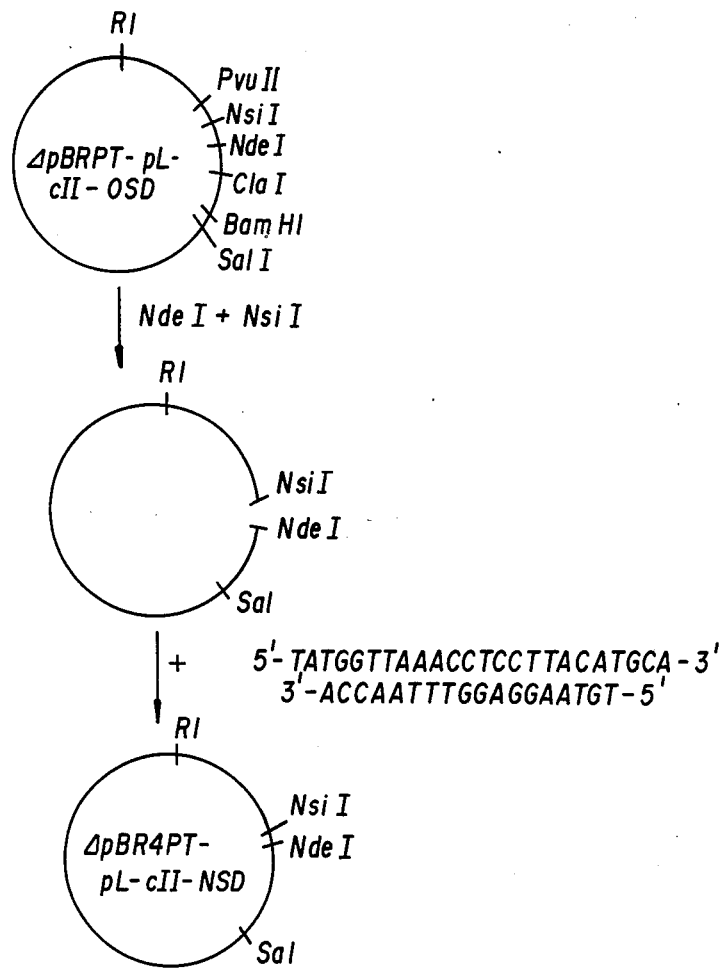
FIG. 9 shows the construction of the plasmid delta pBRPT-pL-cII-NSD from the plasmid of FIG. 8.

FIG. 6 shows the subcloning of the lambda cII Shine-Dalgarno sequencing and coding sequence behind the pL promoter, resulting in plasmid delta pBR4-pL-cII. This plasmid was used in the two step subcloning of essential elements of expression system as Taq 1 fragments. This construction is shown in FIG. 7. The resulting plasmid, delta pBR4-pL-cII-Taq I was then digested with the restriction endonucleases Bam and Sal I. After digestion, the translation polyterminator was added, as shown in FIG. 8. The resulting plasmid was designated delta pBR4PT-pL-cII-OSD. "OSD" designates the "old Shine-Dalgarno" sequence. The "OSD" plasmid was modified then, in parallel with the plasmid, delta pBRPT-pL-cII-NSD, which waas constructed from the "OSD" plasmid, but contains "new Shine-Dalgarno" sequences, as shown in FIG. 9.

Figure 10:
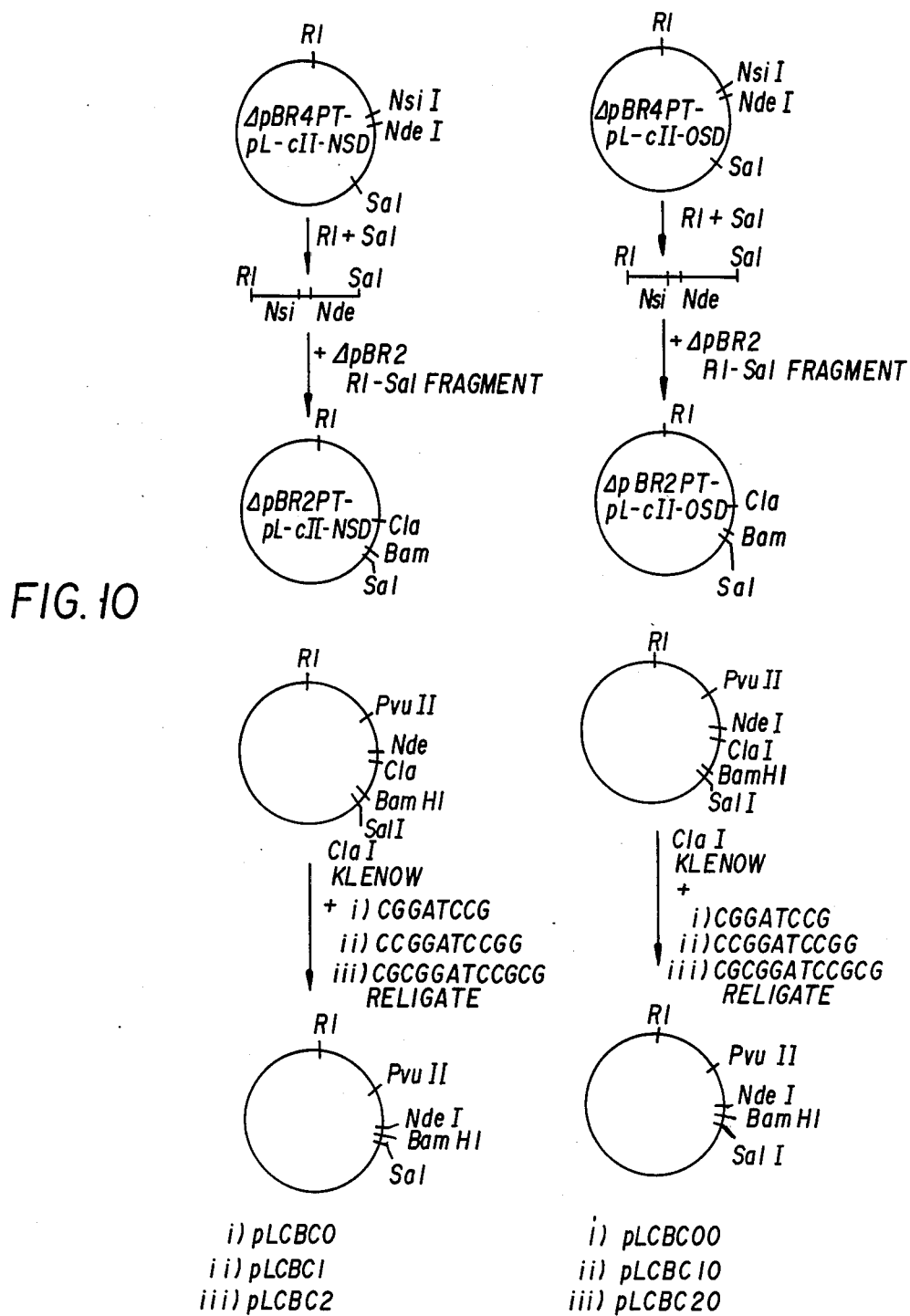
FIG. 10 shows the construction of the plasmids pLCBC0, pLCBC1, and pLCBC2 from the plasmid delta pBR4PT-pL-cII-NSD and the construction of the plasmids pLCBC00-pLCB10, and pLCBC20 from the plasmid delta pBR4PT-pL-cII-OSD.

The expression sequences of the "OSD" and the "NSD" plasmids were subcloned, respectively, into plasmid delta pBR2, as shown in FIG 10. The Cla I site on the resulting plasmids were converted to a BamH1 site, to be used for insertion of the gene fragment to be expressed. The BamH1 site is present in a different reading frame for each of the three vectors constructed. Plasmids pLCBC0, pLCBC1, and pLCBC2 contain the new Shine-Dalgarno sequence. Plasmids pLCBC00, pLCBC10, and pLCBC20 are identical to the above-mentioned plasmids, but contain the original cII Shine-Dalgarno sequence.

EXAMPLE 3

Random Cloning and Direct Cloning Strategy

Expressing clones were generated using a random cloning strategy and a direct cloning strategy.

Random Cloning Strategy

For the random cloning strategy, DNA of two HTLV-III subclones, BH5 and BH8 was partially digested with either AluI or HaeIII and the ends of the resulting fragments randomized with respect to reading frames of a brief digestion with Bal31 exonuclease. These fragments were then cloned into the SmaI site of plasmid pORF1 (Weinstock et al, *Proc. Nat'l. Acad. Sci.*, 80: 4432-4436 (1983)). (pORF$_1$ and pORF$_2$ are deposited in the American Type Culture Collection under ATCC Nos. 39147 and 39145, respectively.) pORF1 contains DNA sequences encoding an OMP promoter and leader peptide, a polylinker, and beta-galactosidase. The random cloning strategy is depicted in FIG. 11. The reading frame for beta-galactosidase is different than that for the OMP-leader peptide. Functional beta-gal (indicated as blue colonies on X-gal plates) will be produced only if a DNA fragment is cloned that contains an open reading frame and realigns the OMP-+beta-gal frames. The protein encoded by this cloned DNA must also be expressed as part of an OMP-beta-gal tripartate fusion protein.

The randomized fragments cloned into the SmaI digested pORF1 transformed *E. coli*, MH3000, hosts, were grown on X-gal plates. Blue and white colonies appeared, and the blue colonies selected. Protein extracts were prepared from the blue colonies. Five positive clones were obtained after evaluating the protein extract using Western blot analysis with AIDS patient sera. The BamHI fragments were isolated from each of these five clones and the fragments cloned into pJLB0. The protein produced from this clone was analyzed by Western immunobolt using AIDS patient sera.

Direct Cloning Strategy

Figure 12:
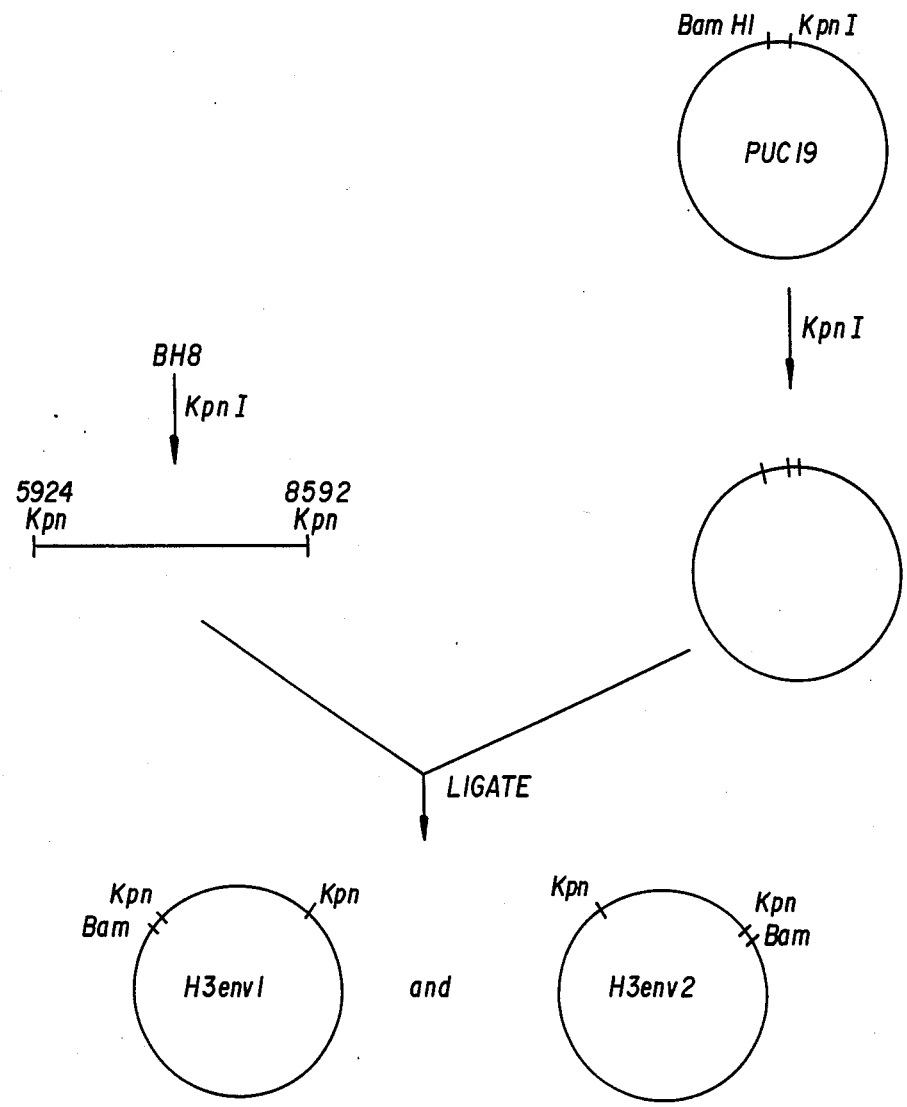
FIG. 12 shows the direct cloning strategy for expressing clones.

For the direct cloning strategy, two additional subclones were prepared by subcloning the Kpn1 fragment of BH8, nucleotides 5924-8592, into PUC 19. (Yarnish-Perron, et al., *Gene*, 26: 101-106 (1983) (PUC 19 is deposited in the American Type Culture Collection under ATCC No. 37254), H3env1, one of the resulting subclones, has the BAMH1 site of PUC 19 adjacent to the Kpn1 site, nucleotide no. 5929 in BH8, and H3env2 has the BamH1 site adjacent to the other Kpn1 cite, nucleotide no. 8597. The direct cloning strategy is shown in FIG. 12.

A number of restriction fragments were isolated after digestion of H3env1, H3env2, and BH8 with BamH1 and/or BglII. These restriction fragments are depicted in FIG. 13. These fragments were cloned into pJLB0T, pJLB1T, or pJLB2T as appropriate for proper reading frame alignment. Translation terminated with the HTLV termination codon for clones C and D, and in the polyterminator for all other clones. Protein expression and immunoreactivity was assayed by gel electrophoresis and Western blot.

EXAMPLE 4

Immunoreactive HTLV-III Expressing Clones

Table I lists the HTLV-III nucleotide fragments that were cloned for expression of HTLV-III peptides in the appropriate vector from the pJL plasmid series. Peptides produced by expressing clones were screened for immunoreactivity against antibodies to the HTLV-III virus from human patient sera. Immunoreactivity with expressed protein from envelope (env) clones A and E was barely detectable with the strongest sera tested and therefore these clones were not tested further. Clones B, C, and D were severely toxic to the host cells, *E. coli*. Since expressed HTLV-III protein from these clones was barely detectable with the strongest sera, they were not tested further.

TABLE I

| | | | | |
|---|---|---|---|---|
| | | HTLV III Expressing Clones | | |
| Name | HTLV-III Nucleotides | Source: Random or Direct | Screened for Immuno-reactivity | Toxic to Host Cell |
| Gag 1 68-10 | 653-1218 | Random; BH5 | + | − |
| Pol 1 60-3 | 2600-3911 | Random; BH5 | + | − |
| Pol 2 57-2 | 2743-4211 | Random; BH5 | + | − |
| A;7.1 | 5928-6986 | Random; BH8 | − Low immunoreactivity | − |
| B;60-25 | 5929-8052 | Direct; H3env1 | − | + |
| C | 8053-8596 | Direct; H3env2 | − | + |
| D;59-9 | 7199-8628 | Direct; BH8 | − | + |
| E;66-1 | 5929-6618 | Direct; H3env1 | − Low immunoreactivity | − |
| F;60-39 | 6619-7198 | Direct; H3env1 | + | − |
| G;66-21 | 7199-8052 | Direct; H3env1 | + | − |

Table I shows the screening results of expressed protein from various clones for immunoreactivity against antibodies to the HTLV-III virus in human patient sera. The first column identifies the name given to the clone, with the second column designating the nucleotide sequence which encodes the expressed peptide fragment. The third column shows the cloning strategy for constructing the clones and the starting material. In the fourth column, the plus sign (+) indicates that expressed protein was screened for immunoreactivity against a panel of HTLV-III positive sera, while those with a minus sign (−) were not screened because of low immunoreactivity with a high titre AIDS sera or because of severe toxicity to the host bacteria. The last column shows which clones were toxic to the transformed host cell; again, the plus sign (+) indicates toxicity to the host cell, while the minus sign (−) indicates that the clones were not toxic to the host cells.

EXAMPLE 5

Sera Evaluation of HTLV-III Clones

HTLV-III peptides from five expressing clones (gag, Pol 1, Pol 2, env F, and env G) were tested for their ability to detect antibodies to HTLV-III virus in human sera. These clones are described in Table I and the experimental results are listed in Table II. Sera tested included both sera positive for the AIDS HTLV-III virus (+) and sera negative for the AIDS HTLV-III virus (−). All sera were characterized based on radioimmune precipitation. The clones were analyzed by Western blot analysis. None of the sera without AIDS HTLV-III antibody reacted with the clones. However, all sera positive for AIDS HTLV-III antibody reacted with envelope (env) G clone.

TABLE II

| | | |
|---|---|---|
| | Evaluation of HTLV-III Clones | |
| Clone | Sera Tested | No. Sera Reacting with Clone |
| gag | 58 + | 33 +, 25 − |
| | 2 − | 2 − |
| pol 1 | 17 + | 14 +, 3 − |
| | 2 − | 2 − |
| pol 2 | 17 + | 14 +, 3 − |
| | 2 − | 2 − |
| env F | 58 + | 37 +, 21 − |
| | 2 − | 2 − |
| env G | 91 + | 91 + |
| | 87 − | 87 − |

HTLV-III peptides from five expressing clones (gag, Pol 1,

TABLE II-continued

Pol 2, env F, and env G) were tested for their ability to detect antibodies to HTLV-III virus in human sera. The expressing clones evaluated are given in the first column, and were previously described in the first and second columns of Table I. In the second column, the first number, followed by a plus sign (+), is the number of patient's sera tested which were known to be positive for antibodies to HTLV-III. The second number, followed by a minus sign (−), is the number of sera tested which were known to be negative, or which did not contain antibodies to HTLV-III.
The third column shows both the specificity and sensitivity of the peptides' ability to detect antibodies to HTLV-III. The best results are shown with clone env G wherein all 91 positive sera tested gave true-positive results and all 87 negative sera tested gave true-negative results. The next two best results are shown with clones pol 1 and pol 2. With these clones, of the 17 positive sera tested, a true-positive result was given in 14 tests, while a false-negative was given in 3 tests. Both negative sera gave true-negative results. With the first clone, gag, of the 58 positive sera tested, a true-positive result was given in 33 tests, while a false-negative result was given in 25 tests. Both negative sera gave true-negative results. The fourth clone, env F, gave similar results.

EXAMPLE 6

Modification for Increased Expression

In order to increase the expression levels of clone G, two different approaches were taken: (i) deleting the DNA encoding two hydrophobic regions of the clone G protein; and (ii) fusing the clone G sequences to other HTLV III sequences that are expressed at high levels.

Clone G contains HTLV-III nucleotides 7199 to 8052. The two hydrophobic regions are approximately encoded by 7350 to 7418 (5′) and 7851 to 7916 (3′). The 3′ hydrophobic region was removed by linearizing H3env1 with BamH1 and removing approximately 200 nucleotides with Bal31 exonuclease. BamH1 linkers were added, plasmids recircularized with DNA ligase. Clones were selected, and designated G-8, G-12, G-29, G-44, G-42, G-46, G-56, G-71, G-79, G-82, and G-84. The new 3′ end points were mapped and ranged from 7500 to 7900. The HTLV-III sequences from these clones were subcloned into expression vector pJLB2T and expression levels determined.

The 5′ hydrophobic region was removed by M-13 site directed mutagenesis using oligonucleotide 5′ TTGTCTGGCCTGTCCTATTCCCAC-3′. This oligo is complementary to nucleotides 7338–7349 and 7419–7430 and will result in the deletion of 23 condons. The deleted nucleotides are nucleotides 7350–7418, inclusive. A properly constructed clone (delta G) was confirmed by hybridization and DNA sequencing and expression level determined.

Double deletions were also constructed between G-8 and G-71. G-8 and G-71 were chosen since their 3′ end points (7840±20 and 7810±20) map near the beginning of the 3′ hydrophobic domain. These double deletions were called delta G-8 and delta G-71 and their expression levels determined.

Clone G waas extended in the 5′ direction to the AhaIII site at nucleotide no. 6827. A BamH1 linker was added at the AhaIII site and expression analyzed (G-A). Double deletions with the Aha extension were also constructed and expression analyzed (delta G-71A and delta G-8A).

Delta G-71A and delta G-8A were also fused to the pol expressing clone, 57-2 as both env-pol and pol-env fusions. HTLV-III DNA fragments from all constructs were subcloned into a plasmid from the pJL expression vector series. E. coli hosts, MZ1, were used to express the peptide fragments. HTLV-III sequences from delta G-71A were then cloned and expressed in three expression vectors: pJLB0T, pLCBC0, and pLCBC00. These clones were designated p-delta-G71A8, p-delta-G71ACN, and p-delta-G71AC. All three clones produced the same protein at the same levels of expression shown in Table III for delta G-71A. p-delta-G71AC is deposited with the ATCC in bacterial host MZ1.

All constructs prepared and analyzed are shown in FIG. 14. Relative expression levels are shown in Table III. The highest expression levels were seen in clones delta G-8, delta G-71, delta G-8A, and delta G-71A.

In summary, neither single deletion or Aha extension increased expression levels significantly. However, both double deletions (delta G-71 and delta G-8) and the Aha extension of these double deletions did dramatically increase expression levels. Pol-delta G-71 fusions produced barely detectable protein levels.

TABLE III

SUMMARY OF EXPRESSION LEVELS*

| Clone | Estimated Expression Level (% of total bacterial protein) |
|---|---|
| G, G-8, G-12, G-29, G-44 G-42, G-46, G-56, G-71, G-79 G-82, G-84, delta G, GA, delta G-A | <0.02% |
| delta G-8, delta G-71 delta G-8A, delta G-71A | 5–10% |
| delta G-71A:pol pol:delta G-71A | <0.005% |

*See FIG. 14 for maps of the noted clones.

EXAMPLE 7

Immunoreactivity of Clones

Immunoreactivity of all clones was tested as follows:
Bacterial cultures were grown in L Broth at 32° C. until OD$_{550}$=0.4. Cultures were then grown at 42° C. for 1 hour. OD$_{550}$ readings were taken and the bacteria harvested by centrifugation. SDS gel loading buffer was added (0.1 ml per 1.5 ml of OD$_{550}$=0.5) and samples placed in a boiling water bath for 5 minutes. Proteins were separated by SDS polyacrylamide gel electrophoresis, blotted onto nitrocellulose and analyzed by reacting with a high titre sera from an AIDS patient, or for screening purposes with sera independently analyzed for HTLV-III antibodies by radioimmune precipitation.

EXAMPLE 8

Protein Purification

High-level expression of desired proteins in bacteria typically results in the formation of insoluble inclusion bodies or aggregates. In order to purify the expressed, recombinant proteins, the solubility of these proteins must be increased. Recombinant protein delta G-71A from HTLV-III expressing clones p-delta-G71A8 or p-delta-G71AC was solubilized and purified as follows:

A culture of E. coli delta G71A was grown in LB Broth at 32° C. to an OD$_{550}$=0.5. The expression of HTLV-III antigens was induced by temperature shift of the culture to 42° C., and incubated at 42° for 90 minutes. The cells were collected by centrifugation at 4000×g for 30 minutes, washed once with TBS and resuspended in 50 mM Tris HCl, pH 8.5, containing 1 mM PMSF, 50 mM DTT, 0.2% Triton X-100, and 10 mM EDTA. The cells were then lysed by enzymatic digestion with lysozyme and brief sonications. The expressed antigen existed as insoluble aggregates and could be collected by centrifugation at 5000×g for 30 minutes. These aggregates were washed several times with mild detergents, and 6M urea. The protein aggregates were solubilized with 8M urea in 50 mM TrisHCl, pH 8.5, containing 1% beta-mercaptoethanol. The free sulfhydryls were alkylated with a 10-fold excess of iodoacetic acid at room temperature. Partial purification of the alkylated antigen was achieved by gel filtration on a sepharose 6B-CL column operated in the presence of 8M urea.

The partially purified antigens were then subjected to citraconylation in borate buffer, pH 8.5, containing 8M urea. This was done by treating the antigen preparation with a 50-fold molar excess of citraconic anhydride at room temperature for 90 minutes. The citraconylated sample was dialyzed extensively against 0.1M borate buffer, pH 8.5, and the antigen was further purified by gel filtration on a Fractogel column equilibrated and eluted with the same buffer.

The citraconylated antigen was eluted from the column in a position corresponding to the elution position of a protein standard with a molecular weight of 30,000, suggesting that the antigen existed in this buffer system as a soluble, monomeric molecule. The fractions devoid of the other protein contaminations were pooled and used for ELISA.

The citraconylated antigen could be absorbed onto microtiter plates and the immobilized antigen remained immunoreactive toward HTLV-III antibodies.

The citraconylated amino groups of the immobilized antigen could be hydrolyzed by the addition of 0.1N acetic acid into each well. Enzyme-linked immunoassay (ELISA) revealed that the immunoreactivity of the deblocked molecules was considerably higher than that of the blocked (citraconylated) molecules as judged by the higher OD value obtained under identical assay conditions.

EXAMPLE 9

ELISA Development

All materials used for ELISA development other than the recombinant protein were provided by Ortho Diagnostics Systems, Inc. Purified delta G-71A was adjusted to a final protein concentration of 0.003 mg/ml in 2M Guanidine HCl, 0.05 m Tris HCl, pH 8.5. 0.1 ml of this antigen was allowed to bind Immulon II microtitre wells for 16 hours at 4° C. The remaining protein solution was removed, wells washed with 2M GuHCl and blocked for 2 hours at 37° C. with 0.1 ml of 10% BSA. Human sera was diluted 1:20 into a final volume of 0.1 ml in Ortho diluent and allowed to bind to the antigen for 1 hour at 37° C. The sera was removed and the wells washed 5×with PBS+0.05% Tween 20. A mouse monoclonal anti-human IgG conjugated with horseradish peroxidase (HRP) was added and allowed to bind for 1 hour at 37° C. The secondary antibody was removed, wells were washed, and substrate solution containing O-phenylenediamine 0.2 HCl (OPD) was added and allowed to react with any bound HRP for 15–30 minutes. The reaction was stopped by the addition of 4N $H_2SO_4$ and $OD_{490}$ read on a Dynatech microtiter plate reader.

Table IV summarizes the ELISA results obtained using the above method. It shows that the ELISA adsorbance values for AIDS and controls did not overlap and that the test reproducibility was acceptable. If a cut-off value of 0.3 was chosen, there would have been no false positives or false-negatives in this group of samples.

Using purified recombinant protein delta G-71A and the procedure above, the anti-HTLV-III samples were also tested provided under the code from the College of American Pathologists (Set WM-B). There were three samples from HTLV-III infected persons that had been diluted in serum from non-infected people. These three samples had OD values no less than 0.70, 0.60, and 0.94 on three separate occasions. Two negative samples scored 0.04 and 0.06. Thus the recombinant protein ELISA was able to easily identify the positive samples.

TABLE IV

Summary of ELISA Results Using Recombinant Protein Delta G71A*

| Clinical Signs | Total Number | Positive For gp 160/120 Ab | Number of Samples with ELISA ($A_{490}$) Values: | | | |
|---|---|---|---|---|---|---|
| | | | Less than .1 | .1 to .3 | .3 to .5 | .5 or greater |
| AIDS/ARC | 94 | 94 (100%) | 0 (%) | 0 (0%) | 2 (2%) | 92 (98%) |
| Non-AIDS | 122 | 0 (0%) | 106 (87%) | 16 (13%) | 0 (0%) | 0 (0%) |

| Sample | UZ,14/30 gp 160/120 Ab | Reproducibility of ELISA Results $A_{490}$ (Individual Assays) | | | | |
|---|---|---|---|---|---|---|
| RC | (+) | 1.4 | 1.8 | 1.7 | 1.7 | |
| O14 | (+) | .60 | .65 | .74 | | |
| SK2-22 | (+) | .63 | .67 | .68 | .67 | |
| SK3-20 | (+) | 1.0 | .56 | .79 | .56 | .80 |
| SK3-5 | (+) | .72 | .60 | .54 | | |
| PD | (−) | .07 | .03 | | | |
| N61 | (−) | .02 | .01 | | | |
| A342 | (−) | .18 | .19 | .19 | | |
| SK4-22 | (−) | .29 | .26 | | | |
| SK4-20 | (−) | .18 | .18 | | | |

*Human sera were obtained from consultants and tested under code for HTLV-III/LAV gp 160/120 antibody (L. W. Kitchen et al, Nature, 312: 367-369 (1984)), and for reactivity with delta G71A in an ELISA test described in Example 9. After the assay results were obtained, the codes were broken.

In testing additional sera using the method described, some control samples gave very high, $OD_{490}$, readings (e.g. 0.60). These samples had no indication of HTLV-III LAV antibody by radioimmune precipitation or Western blots with virus, and were from low risk individuals. Therefore, an improved method was developed.

Purified delta G-71A in 6M GuHCl, 50 mM Tris, pH 8.0 was diluted to 3 ug/ml with 2M GuHCl, 50 mM Tris, pH 8.0 and 100 ul was added to polystyrene wells (e.g. Immulon 2 wells (Dynatech). The antigen was allowed to absorb at 4°–37° C. for 30 minutes to 8 weeks (usually 18 hrs.). The antigen solution was removed from the wells and 100 ul per well of 0.15M NaCl, 10 mM Phosphate, pH 7.3 (PBS) plus 4–10% normal goat serum (NRG) (5% preferred) was added. The wells were then incubated at 30°–39° C. for 30 minutes to 5 hr, 2 hr being preferred.

The PBS & NRG solution was removed and 100 ul per well of 0.5–1.5M NaCl, 10 mM EDTA 10 mM Tris, pH 8.0 (TBS) was added. 5 ul of sera were added and incubated at 18°–39° C. (preferably 37° ) for 15 minutes to 3 hours (1 hr being preferred). The wells were emptied, and washed 4 to 5 times with 0.05% Tween 20 in deionized water. 100 ul per well of mouse monoclonal anti-human IgG conjugated to horseradish peroxidase (Ortho) was added and incubated for 15 min to 1 hour at 20° C. to 39° C. The wells were emptied and washed 4 to 5 times with 0.05% Tween 20 in deionized water. 100 ul per well of 0-phenylenediamine-2HCl substrate in citrate phosphate buffer (Ortho) was added and reacted for 30 minutes at 20°–22° C. 25 ul per well of 4N $H_2SO_4$ was added and the $OD_{490}$ read on a Dynatech microplate reader.

The results with 223 control and 120 AIDS samples are shown in FIG. 20. The highest control value was 0.25 and the lowest AIDS sample was 0.49. Thus there was no overlap between control and AIDS specimens. All the sera used in Example 9 are included in this set. The mean and standard deviation of the control group was 0.05±0.05. Included in the control group were samples which were false-positives on a commercial virus antigen ELISA. More importantly, there were at least 10 AIDS samples, confirmed to be HTLV-III/LAV antibody positive by radioimmune precipitation and Western blots with virus, which were negative by virus ELISA (5 of the samples had an OD less than 0.05, all 10 samples were less than 0.15) but positive by recombinant ELISA (all 10 samples had O.D.'s greater than 0.49).

Although the instant disclosure sets forth all essential information in connection with the invention, the numerous publications cited herein may be of assistance in understanding the background of the invention and the state of the art. Accordingly, all of the publications cited are hereby incorporated by reference into the patent disclosure. Moreover, the foregoing invention has been described in some detail by way of illustration and example for purposes of clarity and understanding. It will be obvious that certain changes and modifications may be practiced within the scope of the invention, as limited only by the scope of the appended claims.

What is claimed is:

1. A peptide fragment which is immunoreactive to antibodies against the HTLV-III virus and is encoded by a nucleotide sequence of the HTLV-III provirus as shown in FIG. 19 from about 7199 to about 7349, about 7419 to about 7850, and about 7917 to about 8052.

2. A peptide fragment which is immunoreactive to antibodies against the HTLV-III provirus and encoded by a nucleotide sequence as shown in FIGS. 18 and 19 from about 6827 to about 7349, about 7419 to about 7850, and about 7917 to about 8052.

3. A peptide fragment which is immunoreactive to antibodies against the HTLV-III virus and is encoded by a nucleotide sequence as shown in FIG. 21 of the HTLV-III provirus from about 6827 to about 6936, about 6952 to about 7349, and about 7419 to about 7802.

4. An antibody raised against a peptide fragment as claimed in any one of claims 1–3.

5. The antibody of claim 4 comprising a monoclonal antibody.

6. A method for the detection of antibodies against the HTLV-III virus comprising contacting a peptide fragment of any one of claims 1–3 with a sample suspected of containing antibodies against the HTLV-III virus and detecting the presence of said antibodies.

7. A method for the detection of HTLV-III virus or portions thereof comprising contacting a sample suspected of containing the HTLV-III virus or portions thereof with an antibody of claim 4 and detecting the presence of said virus.

8. The method of claim 6 comprising immobilizing said peptide fragment on a solid particles selected from the group consisting of latex, gelatin, red blood cells, nylon, liposomes, and gold particles and detecting the presence of said HTLV-III antibodies by the agglutination of said antibodies with said fragment.

9. The method of claim 6 comprising immobilizing said peptide fragment on a solid phase immunoabsorbent and detecting the presence of said HTLV-III antibodies with a detectably labeled antibody which is specific for said peptide fragment or with a detectably labeled anti-antibody to said HTLV-III antibodies.

10. The method of claim 9 wherein said detectably labeled antibody or said detectably labeled anti-antibody is enzyme-labeled and further comprising incubating said peptide fragment immobilized on said solid phase with said sample and with said enzyme-labeled antibody or said enzyme-labeled anti-antibody to allow the components to react; washing to remove unreacted material from said solid phase; and applying to said solid phase an indicator capable of reacting with said enzyme label to produce a detectable enzyme-substrate reaction.

11. The method of claim 7 further comprising a first antibody specific against said HTLV-III virus or portions thereof immobilized on a solid phase immunoabsorbent and a detectably labeled second antibody specific against said HTLV-III virus or portions thereof or a detectably labeled anti-antibody to said first antibody.

12. The method of claim 11 wherein said detectably labeled antibody or said detectably labeled anti-antibody is enzyme-labeled and further comprising incubating said first antibody immobilized on said solid phase with said sample and with said enzyme-labeled antibody or said enzyme-labeled anti-antibody to allow the components to react; washing to remove unreacted material from said solid phase; and applying to said solid phase an indicator capable of reacting with said enzyme label to produce a detectable enzyme-substrate reaction.

13. The method of claim 9 wherein said detectable label is selected from the group consisting of radioactive isotope labels, fluorescent labels, chemiluminescent labels, and bioluminescent labels.

14. The method of claim 11 wherein said detectable label is selected from the group consisting of radioactive isotope labels, fluorescent labels, chemiluminescent labels and bioluminescent labels.

15. A kit for detecting HTLV-III antibodies in a sample comprising a carrier being compartmentalized to receive one or more container means in close confinement therein, a first container means comprising a peptide fragment according to any one of claims 1–3 immobilized on an solid phase immunoabsorbent and a second container means containing a detectably labeled anti-antibody to HTLV-III antibodies.

16. A kit for detecting the HTLV-III virus or portions thereof in a sample comprising a carrier being compartmentalized to receive one or more container means in close confinement therein, a first container means containing a first antibody according to claim 4 immobilized on a solid phase immunoabsorbent and second container means comprising a detectably labeled second antibody according to claim 33 which is cross-reactive with a different domain of the HTLV-III virus from said first antibody or having a detectably labeled anti-antibody to said first antibody.

17. The kit according to claim 15 wherein said kit containing only a first container means comprising said immobilized fragment and wherein the HTLV-III antibodies in said sample causes agglutination.

* * * * *

UNITED STATES PATENT AND TRADEMARK OFFICE
CERTIFICATE OF CORRECTION

PATENT NO. : 4,753,873

DATED : June 28, 1988

INVENTOR(S) : Beltz, et al

Page 1 of 2

It is certified that error appears in the above-indentified patent and that said Letters Patent is hereby corrected as shown below:

In the drawings, Sheet 5, Figure 5, delete "+pBR 322" and substitute therefor: --+ΔpBR4--.

In the drawings, Sheet 6, Figure 6, after "+PvuII DIGESTED" add --ΔpBR4-pL-PvuII--.

In the drawings, Sheet 7, Figure 7, delete "pvaII" and substitute therefor: --pvuII--.

In the drawings, Sheet 12, Figure 12, the plasmid depicted as: 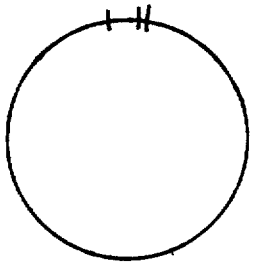 should be depicted as: 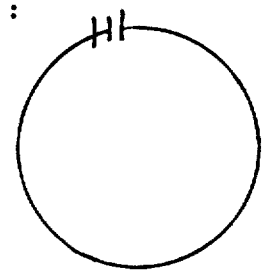

In the drawings, Sheet 21, Figure 21, "BH8/Bh 1 0" should be rewritten as --BH8/BH10--.

In the specification, Column 1, line 34, the word "any" should be written as --an--; Column 12, line 36, the word "sequencing" should be written as --sequence--; Column 13, line 6, the word "of" should be deleted and the word --by-- substituted therefor;

UNITED STATES PATENT AND TRADEMARK OFFICE
CERTIFICATE OF CORRECTION

PATENT NO. : 4,753,873
DATED : June 28, 1988
INVENTOR(S) : Beltz, et al

It is certified that error appears in the above-indentified patent and that said Letters Patent is hereby corrected as shown below:

Column 13, line 9, "pORF1 and pORF2" should be written as --pORF1 and pORF2--.

Signed and Sealed this

Twenty-ninth Day of June, 1993

Attest:

MICHAEL K. KIRK

Attesting Officer

Acting Commissioner of Patents and Trademarks

UNITED STATES PATENT AND TRADEMARK OFFICE
CERTIFICATE OF CORRECTION

PATENT NO. : 4,753,873
DATED : June 28, 1988
INVENTOR(S) : Gerald A. Beltz, et al.

It is certified that error appears in the above-identified patent and that said Letters Patent is hereby corrected as shown below:

On the title page, item [63], under Related U.S. Application Data, please delete "Continuation-in-part of Ser. No. 819,917, Nov. 6, 1985."

Signed and Sealed this

Twenty-first Day of April, 1998

Attest:

BRUCE LEHMAN

Attesting Officer

Commissioner of Patents and Trademarks